(12) United States Patent
Rosenblatt et al.

(10) Patent No.: US 11,298,488 B2
(45) Date of Patent: *Apr. 12, 2022

(54) MONITORING SYSTEM INCLUDING MASK REMOVAL AND OXYGEN DESATURATION PERIOD DETECTION

(71) Applicant: TRUPHATEK INTERNATIONAL LTD., Netanya (IL)

(72) Inventors: David Rosenblatt, Beer Sheva (IL); Moshe Kohen, Bat Yam (IL); Gabriel Dan, Tel Aviv (IL); Tamer Aita, Taybeh (IL); Lilach Sahar, Herzliya (IL)

(73) Assignee: TRUPHATEK INTERNATIONAL LTD., Netanya (IL)

(*) Notice: Subject to any disclaimer, the term of this patent is extended or adjusted under 35 U.S.C. 154(b) by 346 days.

This patent is subject to a terminal disclaimer.

(21) Appl. No.: 16/451,206

(22) Filed: Jun. 25, 2019

(65) Prior Publication Data

US 2019/0318820 A1    Oct. 17, 2019

Related U.S. Application Data

(63) Continuation of application No. 15/511,525, filed as application No. PCT/IB2015/057135 on Sep. 16, 2015, now Pat. No. 10,331,853.

(Continued)

(51) Int. Cl.
*A61B 1/00* (2006.01)
*A61M 16/04* (2006.01)
(Continued)

(52) U.S. Cl.
CPC ..... *A61M 16/0409* (2014.02); *A61B 1/00052* (2013.01); *A61B 1/00055* (2013.01);
(Continued)

(58) Field of Classification Search
CPC ............ A61M 16/0051; A61M 16/01; A61M 16/0488; A61M 16/06; A61M 2202/0208;
(Continued)

(56) References Cited

U.S. PATENT DOCUMENTS 10,331,853 B2 * 6/2019 Rosenblatt ............. G16H 20/40
2003/0078476 A1 4/2003 Hill
(Continued)

FOREIGN PATENT DOCUMENTS

CN       202113456 U    1/2012
EP        1938740 A1    7/2008
(Continued)

OTHER PUBLICATIONS

International Search Report issued in International Patent Application No. PCT/IB2015/057135 dated Jan. 14, 2016. [Cited in related U.S. Appl. No. 15/511,525].
(Continued)

*Primary Examiner* — Eduardo C Robert
*Assistant Examiner* — David C Comstock
(74) *Attorney, Agent, or Firm* — BakerHostetler

(57) ABSTRACT

A method of approximating a position of an oxygen mask during a procedure includes detecting a presence of the oxygen mask based on a signal from a sensor or through an observation through an optical imaging device; determining whether the oxygen mask is close to or on a patient for supplying oxygen to the patient; detecting a removal of the oxygen mask from the patient to stop supplying oxygen to the patient; initiating a desaturation timer in response to the sensor or the optical imaging device detecting the removal of the oxygen mask from the patient; and operating an image display device to display a parameter for the oxygen desaturation timer.

14 Claims, 20 Drawing Sheets

Related U.S. Application Data

(60) Provisional application No. 62/051,152, filed on Sep. 16, 2014.

(51) Int. Cl.

| | | |
|---|---|---|
| *A61B 5/00* | (2006.01) | |
| *A61B 1/267* | (2006.01) | |
| *A61B 5/08* | (2006.01) | |
| *A61B 5/103* | (2006.01) | |
| *A61B 5/145* | (2006.01) | |
| *A61B 5/1455* | (2006.01) | |
| *A61B 5/1459* | (2006.01) | |
| *A61B 1/05* | (2006.01) | |
| *G16H 20/40* | (2018.01) | |
| *G16H 40/63* | (2018.01) | |
| *G16H 30/40* | (2018.01) | |
| *A61M 16/00* | (2006.01) | |
| *A61M 16/01* | (2006.01) | |
| *A61M 16/06* | (2006.01) | |
| *G16H 30/20* | (2018.01) | |

(52) U.S. Cl.
CPC ............... *A61B 1/05* (2013.01); *A61B 1/267* (2013.01); *A61B 5/0075* (2013.01); *A61B 5/0084* (2013.01); *A61B 5/08* (2013.01); *A61B 5/1032* (2013.01); *A61B 5/1459* (2013.01); *A61B 5/14542* (2013.01); *A61B 5/14551* (2013.01); *A61B 5/6852* (2013.01); *A61B 5/7282* (2013.01); *A61B 5/743* (2013.01); *A61M 16/0051* (2013.01); *A61M 16/01* (2013.01); *A61M 16/0411* (2014.02); *A61M 16/0488* (2013.01); *A61M 16/06* (2013.01); *G16H 20/40* (2018.01); *G16H 30/20* (2018.01); *G16H 30/40* (2018.01); *G16H 40/63* (2018.01); *A61B 5/72* (2013.01); *A61B 2505/05* (2013.01); *A61B 2562/0223* (2013.01); *A61B 2562/0247* (2013.01); *A61B 2562/0257* (2013.01); *A61M 2202/0208* (2013.01); *A61M 2205/0272* (2013.01); *A61M 2205/3306* (2013.01); *A61M 2205/3344* (2013.01)

(58) Field of Classification Search
CPC .. A61M 2205/0272; A61M 2205/3306; A61M 2205/3344; A61M 16/0003; A61M 16/04; A61B 1/00052; A61B 1/00055; A61B 1/05; A61B 1/267; A61B 5/08; A61B 5/14551; A61B 5/7282; A61B 5/743; A61B 2505/05; A61B 2562/0257

USPC .............................. 600/188, 194; 128/207.14

See application file for complete search history.

(56) References Cited

U.S. PATENT DOCUMENTS

| | | | |
|---|---|---|---|
| 2006/0004258 A1 | 1/2006 | Sun et al. | |
| 2006/0150974 A1* | 7/2006 | Berthon-Jones | A61M 16/0003 128/204.21 |
| 2007/0106122 A1 | 5/2007 | Yokota et al. | |
| 2008/0300464 A1 | 12/2008 | Dhingra et al. | |
| 2011/0130627 A1 | 6/2011 | McGrail et al. | |
| 2011/0196251 A1* | 8/2011 | Jourdain | A61M 16/0057 600/538 |
| 2011/0263935 A1 | 10/2011 | Qiu | |
| 2013/0032153 A1 | 2/2013 | Neely | |
| 2013/0237763 A1 | 9/2013 | Qiu | |
| 2013/0303849 A1 | 11/2013 | Allyn et al. | |
| 2015/0157817 A1 | 6/2015 | Steiner, III | |
| 2015/0265794 A1* | 9/2015 | De Kruyff | B29C 64/106 128/200.23 |
| 2016/0022140 A1* | 1/2016 | Colman | A61B 5/746 340/539.12 |
| 2016/0029973 A1* | 2/2016 | Kahlman | A61B 5/015 600/301 |

FOREIGN PATENT DOCUMENTS

| | | |
|---|---|---|
| EP | 2710948 A1 | 3/2014 |
| JP | 2002345781 A | 12/2002 |
| JP | 2005-157902 A | 6/2005 |
| WO | 02/096282 A2 | 12/2002 |
| WO | 2014126457 A1 | 8/2014 |

OTHER PUBLICATIONS

International Search Report issued in International Patent Application No. PCT/IB2015/057136 dated Jan. 14, 2016.

Kuo Chung-Feng Jeffrey et al: "Using image processing technology and mathematical algorithm in the automatic selection of vocal cord opening and closing images from the larynx endoscopy video", Computer Methods and Programs in Biomedicine, vol. 112, No. 3, Dec. 1, 2013 (Dec. 1, 2013), pp. 455-465.

\* cited by examiner

MONITORING SYSTEM INCLUDING MASK REMOVAL AND OXYGEN DESATURATION PERIOD DETECTION

CROSS-REFERENCE TO RELATED APPLICATIONS

This application is a continuation of U.S. patent application Ser. No. 15/511,525, filed Mar. 15, 2017, which is a National Stage Entry of PCT/IB2015/057135, filed Sep. 16, 2015, which claims the benefit of U.S. Provisional Application No. 62/051,152, filed Sep. 16, 2014, the entire contents of which are hereby incorporated herein by reference.

BACKGROUND

Intubation is a standard practice involving insertion of a tube into a trachea providing oxygen to a patient during surgery. A standard procedure for direct intubation of patients involves manipulating a patient to give a clinician performing an intubation a direct line of sight of the patient's larynx, so as to guide an intubation tube properly into the patient's trachea. In some cases, obtaining a direct line of sight cannot be achieved and a video image originating from the tip of an intubation device is used to identify airway landmarks and help guide the tube through the larynx.

Intubations must be completed within a narrow time window after a patient has been pre-oxygenated and breathing has been stopped during which time there is no oxygen supply until the tube is in place and begins to provide oxygen. Failure to properly place the tube in a short time can lead to aborting the planned operation and risk the patient's health. In the case of pre-oxygenation, the time when oxygen supply is cut off occurs when a face mask providing an oxygen supply is removed. The recommendation for allowed time can range from 30 seconds per try to up to several minutes depending on the situation.

During an intubation procedure, there is a risk that a clinician could be unaware or loses track of one or both of the time since an oxygen supply has been cutoff from a patient, and an oxygen saturation level of the patient. In the case of the latter, oxygen levels of the patient may be available from other devices, but require the clinician to look at the other device and divert the clinician's focus from the patient and the physical acts involved with the intubation procedure.

SUMMARY

The foregoing needs are met by the present invention, wherein according to certain aspects, a method of indicating a oxygen desaturation period has been initiated includes detecting, via at least one of an optical imaging device and one or more sensors, an oxygen mask configured to supply oxygen to a patient to saturate the patient, detecting, via the at least one of the optical imaging device and the one or more sensors, a removal of the oxygen mask from the patient to stop saturation of the patient, initiating, via one or more processors, a desaturation timer in response to the at least one of the optical imaging device and the one or more sensors detecting the removal of the oxygen mask from the patient, and operating, via the one or more processors, an image display device to display a first running time indicating a desaturation time elapsed from a time of the removal of the mask.

In accordance with other aspects of the present disclosure, at least one of an optical imaging device and one or more sensors includes one or more stationary proximity sensors, an oxygen mask includes one or more magnets creating a permanent magnetic field, and the oxygen mask is positioned to saturate a patient and the one or more stationary proximity sensors are located in the permanent magnetic field according to a method of indicating an oxygen desaturation period has been initiated.

In accordance with other aspects of the present disclosure, a method of indicating an oxygen desaturation period has been initiated includes receiving, via the one or more processors, a position of the oxygen mask according to an operation of one or more stationary proximity sensors and the one or more magnets, determining, via the one or more processors, a distance between the oxygen mask and one of the location and the one or more stationary proximity sensors according to the position of the oxygen mask, and comparing, via the one or more processors, the position of the oxygen mask to a first threshold distance. Detecting the removal of the oxygen mask includes detecting the movement of the oxygen mask in response to the one or more processors determining, based on the comparing, the oxygen mask is positioned a first distance from the one of the location and the one or more stationary proximity sensors greater than the first threshold distance.

In accordance with other aspects of the present disclosure, a method of indicating an oxygen desaturation period has been initiated includes determining, via the one or more processors, a second distance between the oxygen mask and the one of the location and one or more stationary proximity sensors prior to the detecting the removal of the oxygen mask, setting, via the one or more processors, a second threshold according the second distance, and resetting, via the one or more processors, the timer and stopping the display of the first running time in response to the one or more processors determining the oxygen mask is positioned a third distance from the one or more stationary proximity sensors that is less than the second distance.

In accordance with yet other aspects of the present disclosure, at least one of an optical imaging device and one or more sensors includes one or more pressure sensors attached to the oxygen mask, and detecting a movement of a mask includes detecting the movement of the oxygen mask in response to one or more pressure sensors detecting a change in pressure for a supply of oxygen by the oxygen mask greater than a threshold pressure change for a method of indicating an oxygen desaturation period has been initiated.

In accordance with yet other aspects of the present disclosure, at least one of and optical imaging device and one or more sensors includes an optical imaging device, the optical imaging device is focused on a location including the oxygen mask positioned on the patient, and detecting a removal of the oxygen mask includes detecting the removal of the oxygen mask in response to the oxygen mask being removed from a location according to an image from the optical imaging device for a method of indicating an oxygen desaturation period has been initiated.

In accordance with other aspects of the present disclosure, operating an image display device includes operating the image display device to display a running time in a position on a screen that corresponds to a location within a field of view from a first location that is a working distance of 50 cm from a second location defining a focus of the field of view, and the field of view is 10° and the second location does not coincide with a position on the screen for a method of indicating an oxygen desaturation period has been initiated.

In accordance with yet other aspects of the present disclosure, a method of indicating an oxygen desaturation period has been initiated includes determining, via the one or more processors, an intubation procedure has been initiated according to a position of an intubation device assembly, and operating, via the one or more processors, an image display device to display a first running time and a second running time indicating an elapsed time from the intubation procedure being initiated.

In accordance with still other aspects of the present disclosure, a method of indicating an oxygen desaturation period has been initiated includes receiving, via one or more processors, data from a first oxygen sensor configured to be attached to a patient and data from a second oxygen sensor of an anesthesia machine, determining, via the one or more processors, a differential between a first oxygen level corresponding to the data from the first oxygen sensor and a second oxygen level corresponding to the data from the second oxygen sensor to a deviation threshold, and operating, via the one or more processors, an image display device to display the first level of oxygen in response to the differential being less than the deviation threshold.

In accordance with still other aspects of the present disclosure, a method of indicating an oxygen desaturation period has been initiated includes detecting, with one or more position sensors, an orientation of the screen of the imaging device, setting, with the one or more processors, a template for displaying the first running in the display window on the screen according to the orientation of the screen and a first field of view from a first location focused on a second location that does not coincide with a location of the screen, and operating, with the one or more processors, the image display device to display the display window including the running time and a video image from an optical imaging device of the intubation assembly on the screen.

In accordance with yet other aspects of the present disclosure, setting a template includes setting a position of a display window to be within a first field of view such that at least a portion of a display window is positioned in an area of a screen surrounding a display of a video image and including a background of a single color in, a method of indicating an oxygen desaturation period has been initiated.

In accordance with yet other aspects of the present disclosure, a system includes an intubation device assembly including an intubation device, and an image display device including a screen and a controller. The system includes a proximity sensor configured to communicate with the controller, and a magnet configured to provide a permanent magnetic field. The magnet is positioned more than a predetermined distance from the proximity sensor and the controller initiates a timer and operates the image display device to display a running time on the screen indicating an elapsed time from the initiation of the timer.

In accordance with yet other aspects of the present disclosure, a system includes at least one oxygen sensor configured to detect an oxygen saturation and communicate with the controller. A magnet is positioned more than the predetermined distance from a proximity sensor and a controller operates an image display device to display a running time and the oxygen saturation on a screen.

There has thus been outlined, rather broadly, certain aspects of the present disclosure in order that the detailed description herein may be better understood, and in order that the present contribution to the art may be better appreciated.

In this respect, before explaining at least one embodiment of the present disclosure, it is to be understood that the present disclosure is not limited in its application to the details of the construction and to the arrangements of the components set forth in the following description or illustrated in the drawings. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

DETAILED DESCRIPTION

Aspects of the disclosure will now be described in detail with reference to the drawings, wherein like reference numbers refer to like elements throughout, unless specified otherwise.

It is noted that as used in the specification and the appending claims the singular forms "a," "an," and "the" can include plural references unless the context clearly dictates otherwise.

Unless specified otherwise, the terms "substantial" or "substantially" as used herein mean "considerable in extent," or "largely but not necessarily wholly that which is specified."

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Figure 1A:
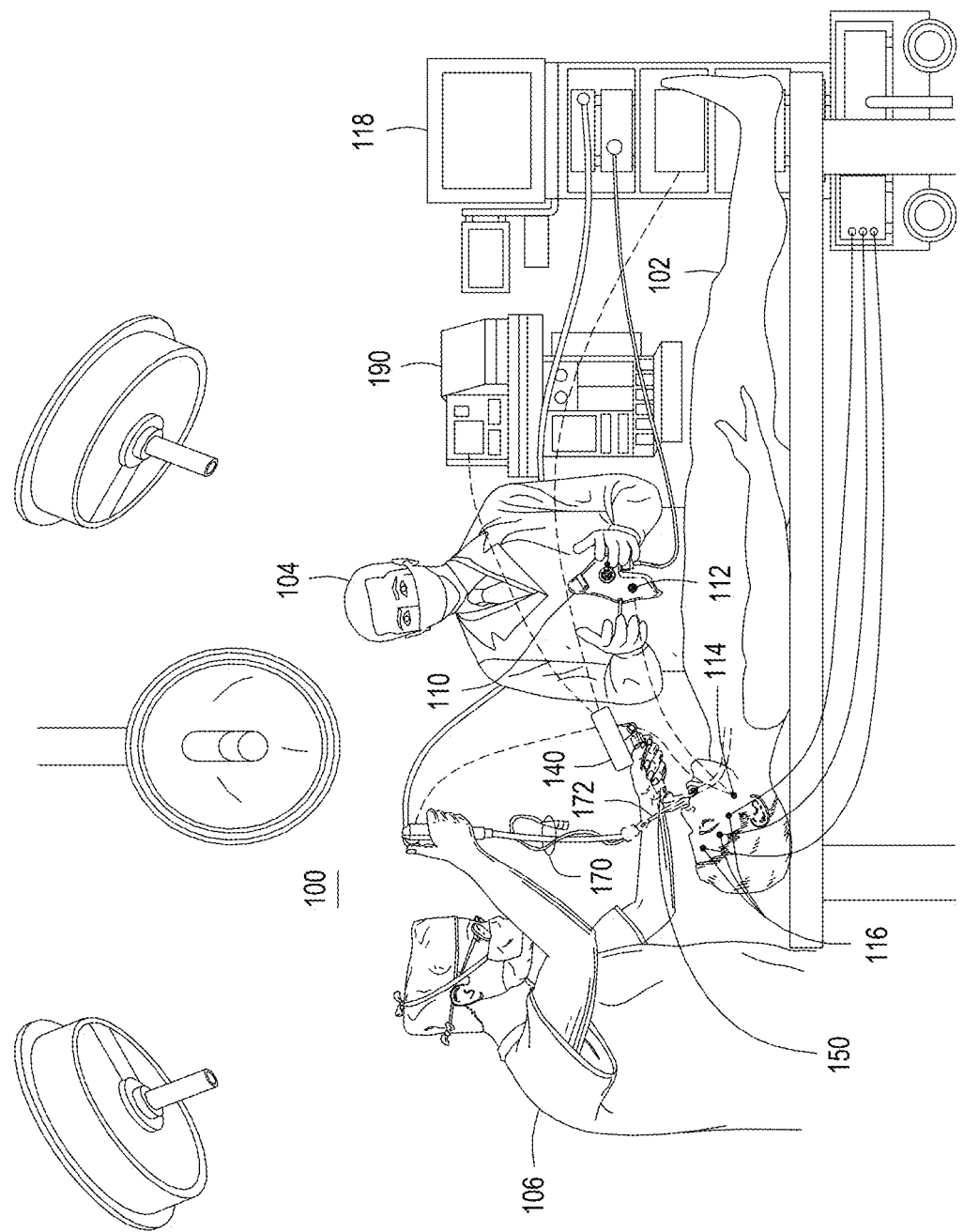
FIG. 1A illustrates a medical procedure involving an intubation device, according to an aspect of the present disclosure.

FIG. 1A illustrates a medical procedure, according to one aspect of the present disclosure. In a room 100, a patient 102 is attended to by a first clinician 104 and a second clinician 106. The first clinician 104 is holding a mask 110, e.g. an oxygen mask, which includes a magnet embedded in the mask 110. The magnet 112 may be small in size relative to the mask 110. It will be appreciated that the mask 110 may include more than one magnet 112 embedded in the mask 110. A permanent magnetic field of the magnet 112 produced according to the Hall effect may be detected with one or more stationary proximity sensors 114 (hereafter referred to as "proximity sensors 114") which are attached to a head of the patient 102. The proximity sensors 114 may detect the permanent magnetic field in order to detect a change of distance from the magnet 112 to the proximity sensors 114, and thereby detect a removal of the mask 110 from the patient 102. Each proximity sensor 114 can be attached to the patient 102 via an adhesive patch.

Also attached to a head of the patient 102, is at least one $SpO_2$ sensor 116 (hereafter referred to as "oxygen sensor 116") which measures oxygen saturation and pulse. There may be a plurality of oxygen sensors 116 attached to the head (e.g. lip, nose, forehead, etc.) and body of the patient 102. The oxygen sensors 116 may communicate or be connected to an anesthesia machine 118. It will be appreciated that other $SpO_2$ sensors may be located on other parts of a body of the patient 102. According to an aspect of the present disclosure, the oxygen sensors 116 which include facial oxygen sensors may be combined with the proximity sensors 114. More specifically, lip, nose, and forehead sensors may include proximity sensors 114 to detect a position of mask 110 and be monitored to generate events related to pre-oxygenation time and start of desaturation. The oxygen sensors 116 may be provided with different types of oxygen monitoring equipment available from manufactures such as Nonin® or Masimo, and capable communicating wirelessly via Bluetooth or NFC.

The second clinician 106 is holding an intubation device 150 in one hand and the tube or coaxial arrangement of tube devices 170 including a stylet 172 (e.g. a video stylet), in the other hand. The tube or coaxial arrangement of tube devices 170 may include the stylet 172 and, for example a tube including a cuff (e.g. an endotracheal tube), and/or an exchanger tube. An image display device 140 is attached to the intubation device 150, which includes an optical imaging device (not shown) configured to transmit a video image of an area encompassed by a field of view of the optical imaging device (i.e. an optical field of view of the optical imaging device). The image display device 140 may be any type of monitor or other image display, and may be a touch sensitive monitor. The image display device 140 may communicate with the proximity sensor 114, the oxygen sensor 116, the anesthesia machine 118, the intubation device 150 and the tube or coaxial arrangement of tube devices 170 via various types of wireless communication protocols such as Wi-Fi, Bluetooth, Near Field Communication (NFC), etc. The image display device 140 may also communicate with a computing system 190 positioned in the room 100, which may be in communication with a central information system (not shown) of for example a hospital.

Figure 1B:
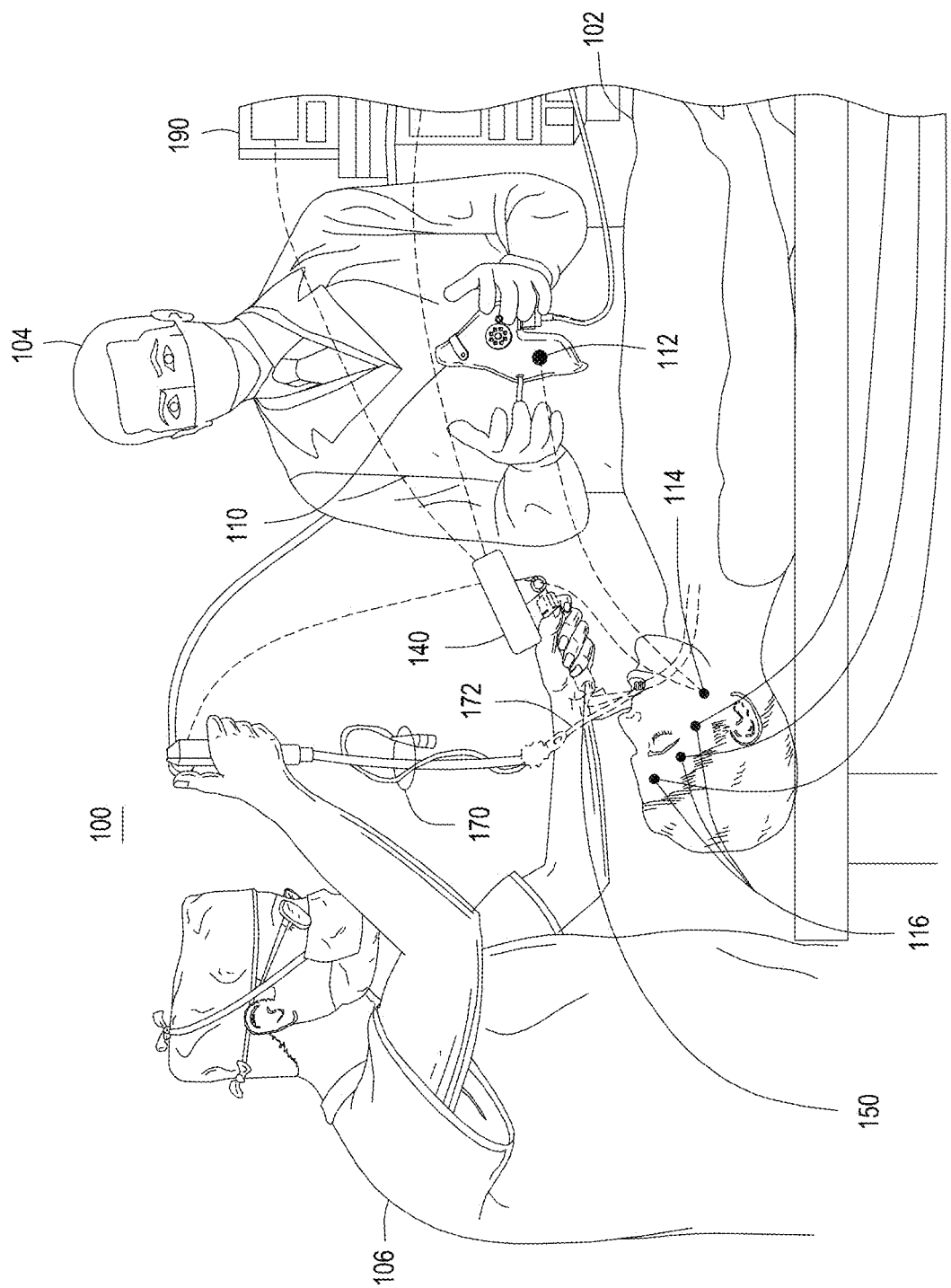
FIG. 1B illustrates an enlarged portion of FIG. 1A.

FIG. 1B illustrates an enlarged portion of FIG. 1A. As can be seen from FIG. 1B, the intubation device 150 is inserted into the mouth of the patient 102 to extend into the throat of the patient 102. The intubation device 150 may be a laryngoscope or a laryngeal mask airway, or other known device utilized for intubation procedures.

Figure 2:
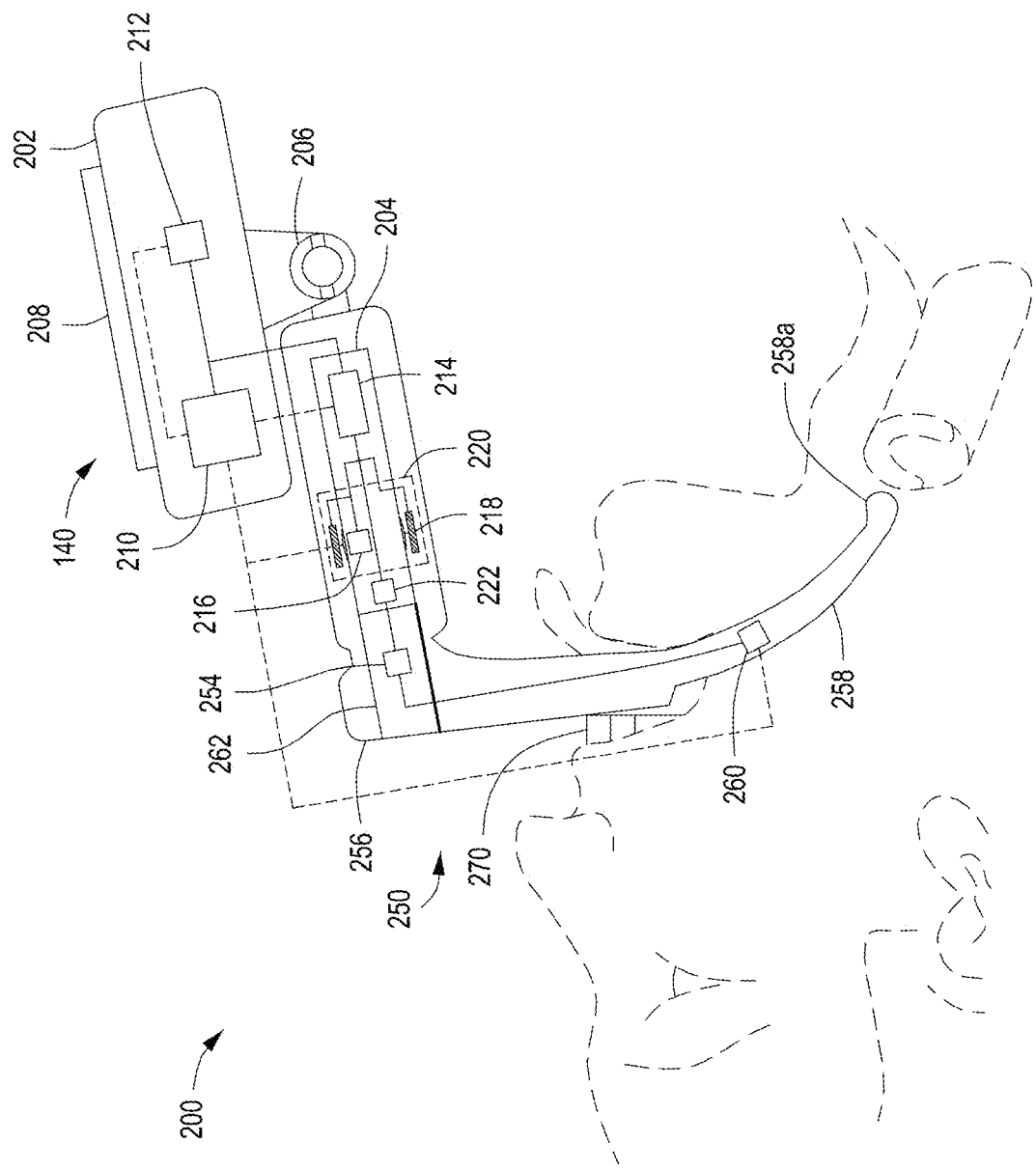
FIG. 2 illustrates a schematic view of an intubation device assembly, according to an aspect of the present disclosure.

FIG. 2 illustrates a schematic view of an intubation device assembly 200, according to an aspect of the present disclosure. The intubation device assembly 200 includes the image display device 140, and an example of a type of the intubation device 150 of FIGS. 1A and 1B. Specifically, an intubation device 250 which defines a laryngoscope. The image display device 140 includes a housing 202 connected to a main cartridge 204 by a connection joint 206. A screen 208 of the image display device 140 is positioned on a side of the housing 202 opposite to the connection joint 206, and may include a liquid crystal display (LCD), organic light-emitting diode (OLED), active-matrix organic light-emitting diode (AMOLED). Within the housing 202, a controller 210 may be in operative communication with a first position sensor 212 that may be positioned on an exterior surface of the housing 202, within a recess in the exterior surface of the housing 202, or within the housing 202. The controller 210 may be connected to a power source 214, such as in the form of a rechargeable or disposable battery.

It will be appreciated that the main cartridge 204 may be interchangeably connected to the housing 202 of the image display device 140. Accordingly components in the main cartridge 204 may be provided in different arrangements in versions of the main cartridge 204 having a different shape and size.

The main cartridge 204 may be received in a handle 252 of the intubation device 250, and the first connector 222 may engage a second connector 254 positioned on a head 256 of a blade 258. The blade 258 and handle 252 together provide a laryngoscope. Accordingly, the blade 258 of the laryngoscope may be used to depress a tongue of the patient 102, to clear a path for an object (e.g. a tubular object such as a stylet, endotracheal tube, or combination thereof) into a trachea of the patient 102. By the connection between the first connector 204 and the second connector 254, an optical imaging device 260 is operatively connected to the controller 210 and supplied with power from the power source 214. The optical imaging device 260 may be a camera including an LED, or other type of device that may transmit an optical signal to the controller 210 providing a optical field of view that includes a view of the area downstream of the blade 258 (e.g. an area adjacent to a larynx of the patient 102 during a procedure). For example, the optical imaging device 260 may be a System On Chip (SOC) with video processing capability. The optical imaging device 260 is located near a distal tip 258a of the blade 258 and connected to a fiber optic cable.

The intubation device 250 may be used to position the tube or coaxial arrangement of tube devices 170 in the patient 102. During a procedure in which the intubation device 250 is positioned into the patient 102, the handle 252 and or cartridge 212 may be orientated together or relative to each other according to a force exerted by an operator (e.g. a clinician) and a reactive force applied by physical boundaries defined by an anatomical structure of the patient 102. Further, the entire intubation device assembly 200 may have to progress through multiple positions in order to correctly position the blade 258 within the patient 102. Through this process, the structures of the blade 258, head 256, and even handle 252, my come in contact with the patient 102 applying a force to the patient 102.

The second position sensor 216 may detect an orientation of the intubation device assembly 200. According to an aspect of the present disclosure, the second position sensor 216 may include an accelerometer which may convert a signal from electric elements, such as a piezoelectric strip or a capacitor, into a voltage that can be measured in order to determine an orientation of the image display device 140 and thus the intubation device assembly 200. An accelerometer of the second position sensor 216 may output an analog or a digital signal.

When the main cartridge 204 is received by a load bearing column 262 and rigidly attached thereto, as a result of being inserted into the handle 252. The load bearing column 262 extends from the head 256 of the blade 258, and the force sensors 218 engage an inner wall 264 of the handle 252. Accordingly, movement of the handle 252 relative to the load bearing column, and thus the cartridge 204, may be transmitted to the force sensors 218. According to another aspect of the present disclosure, the force sensors 218 may be tactile or surface sensors that change due to pressure applied thereto. The force sensors 218 may detect a mechanical load, e.g. a force, pressure, moment, being applied, for example as a reactive force, when the handle 252 is pressed against an object. Thus the force sensors 218 determine a force, pressure, or moment, applied to the cartridge 204 which is proportional to the force applied by the handle 252 to an external object, for example teeth of the patient 102.

As described in further detail below with respect to FIG. 15, the accelerometers provided as the second position sensor 216 and the force sensors 218 may be used to measure a force applied to the teeth 270 of the patient 102 during a procedure in which the blade 258 is inserted into the patient's mouth. Obtaining information related to an orientation of the intubation device 250 and a force being applied to the patient 102 may be used to more efficiently position the blade 258 of the intubation device 250 in the patient 102 while reducing the amount or force to which the patient 102 will be subjected.

Figure 3:
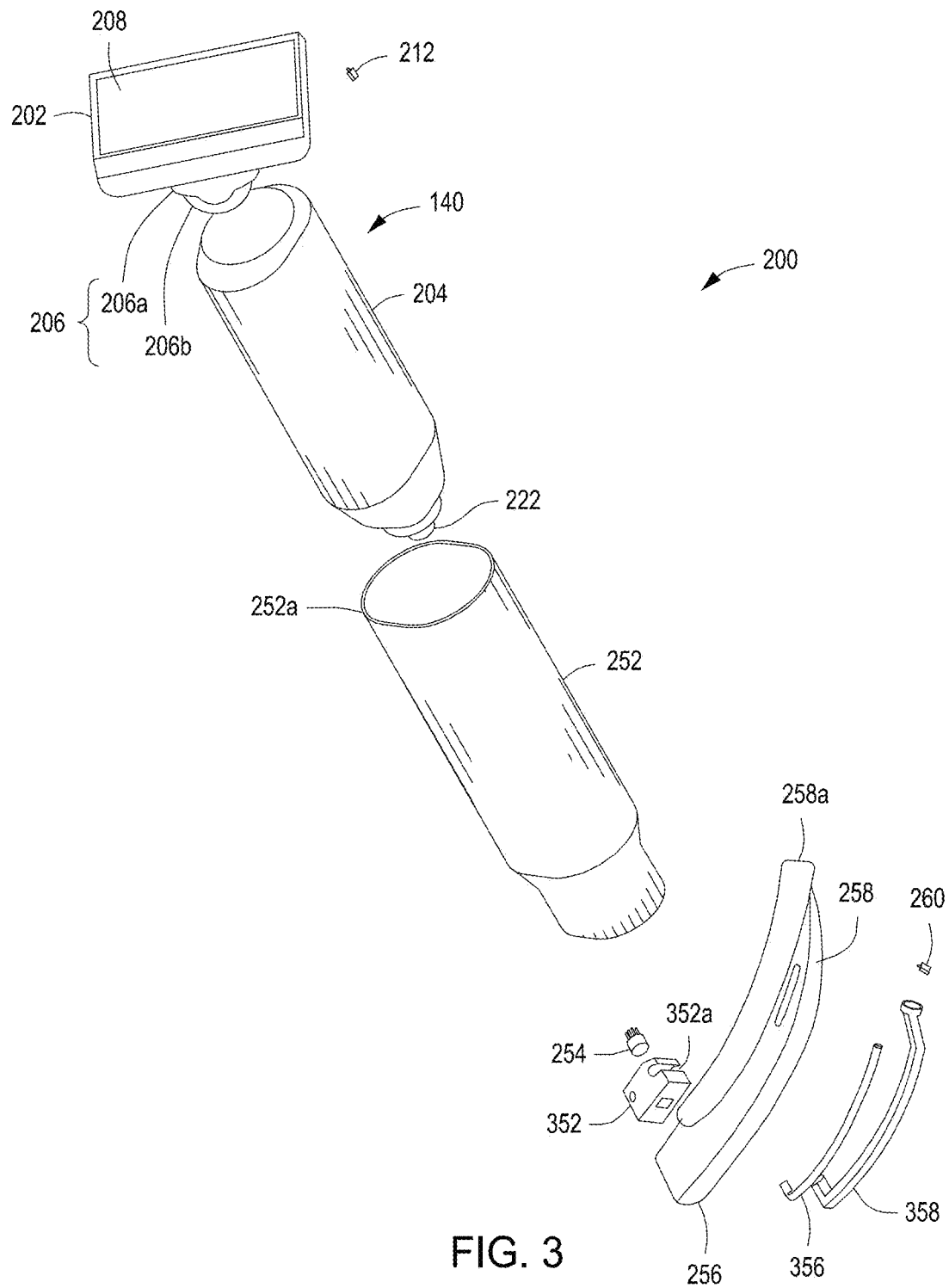
FIG. 3 illustrates an exploded view of the intubation device assembly of FIG. 2.

FIG. 3 illustrates an exploded view of the intubation device assembly 200 of FIG. 2. The cartridge 204 includes the first connector 222 at one end, and a ball 206b of the joint connection 206 that is received in a socket 206a extending from the housing of the image display device 140. The image display device 140 may be pivoted about the ball 206b by an operator in order to be placed in an optimal position during a procedure.

The head 256 of the intubation device is connected to a removable mounting slot 352 which includes the second connector 252 which connects to the first connector 222 when the cartridge 204 is inserted into the handle 252. According to an aspect of the present disclosure, an end of the handle attached to the blade 258 may include a bracket with a cylindrical rod (not shown) extending between inner surfaces of the bracket of the handle 252. The mounting slot 352 may be positioned with the head 256 of the blade 258 and receive the cylindrical rod in a slot 352a formed therein. The second connector 254 may be provided on a surface, or within a recess on a surface of the mounting slot 352 and connect to the first connector 254 when the blade is rotated away from the handle 252 so as to form a substantially right angle with the handle 252.

The connection between the first connector 222 and the second connector 254 may provide a connection between the power source 214 and/or the controller 210 and the optical imaging device 260 positioned on the blade 258 relative to the head 256. According to an aspect of the present disclosure, an intermediate connector may be provided an on inner surface of the handle 252 facing the first connector 222 of the main cartridge 204. The intermediate connector may extend to an outer surface of the handle 252 which faces the mounting slot 252 when the blade 258 is attached to the handle. Accordingly, the intermediate connector may be connected with both of the first connector 222 and the second connector 254 and provide the connection between the power source 214 and/or the controller 210 and the optical imaging device 260.

The optical imaging device 260 is attached to an electrical cable 356 which is held in place by a plastic cover 358 that attaches to the blade 258. The optical imaging device 260 is mounted to the end of the plastic cover 358.

Figure 4:
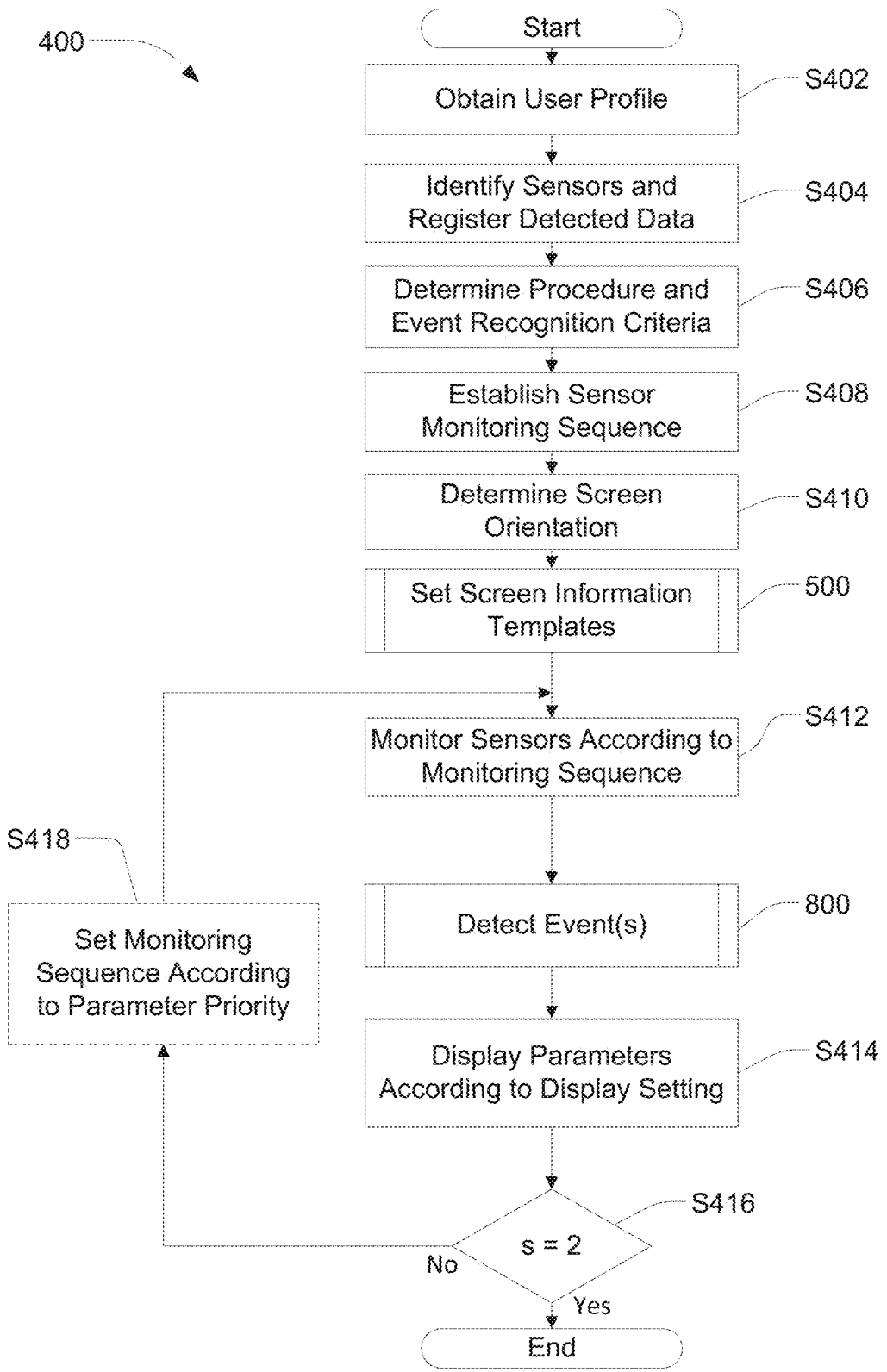
FIG. 4 is an algorithmic flowchart illustrating a method of operating an image display device according to an aspect of the present disclosure.

FIG. 4 is an algorithmic flowchart illustrating a method of operating an image display device 400 according to an aspect of the present disclosure. For illustration, the operations of the method of operating an image display device 400 will be discussed in reference to FIGS. 1-3. In block S402, the controller 210 obtains a user profile of an operator using the image display device 140 during a procedure.

The controller 210 identifies each sensor in an array of sensors the image display device 140 is configured to communicate with in block S404. In the case of the intubation device assembly 200, the controller 210 identifies the screen 208 which may be touch sensitive, the first position sensor 212, the second position sensor 216, the force sensor 218, and the optical imaging device 260 at least with a connection of the first connector 222 and the second connector 254. It will be appreciate that the controller 210 may be physically connected to each of the screen 208, the first position sensor 212, the second position sensor 216, the force sensor 218, the optical imaging device 260, the first connector 222, and the second connector 254. Alternatively, the optical imaging device 260 may communicate with the controller 210 via Wi-Fi, Bluetooth, or NFC. Data from these sensors is obtained by the controller 210 in order to identify and register the types of data that will be provided by the sensors.

In block S406, the controller 210 may analyze the data obtained from sensors in communication therewith, and establish respective criteria for recognizing events. In block S408, the controller 210 may establish a sensor monitoring sequence, which may be based on a predetermined priority of the data being obtained, or may be set by an operator before a procedure begins. A screen orientation of the image display device 140 is determined in block S410. Specifically, the controller 210 may communicate with the first position sensor 212 to determine a position relative to the patient 102, and communicate with the second position sensor 216 to determine an overall orientation (e.g. angle) of the image display device 140, and thus an orientation of the intubation device assembly 200 in which the cartridge 204 is received.

Following block S410, the controller 210 controls the image display device 140 according to a screen information template setting algorithm 500, which is described in further detail with reference to FIG. 5. In block S412, the controller 210 monitors the proximity sensor 114, the oxygen sensor 116, the anesthesia machine 118, the first position sensor 212, the second position sensor 216, the force sensor 218, and the optical imaging device 260 according to the sequence determined in block S408. It will be appreciated that readings/image data from the sensors/optical device (114, 116, 212, 216, 218, 260) are continuously obtained and available for evaluation by the controller 210. As described in more detail with respect to FIG. 8, where a desaturation timer $t_S$ has been initiated, the controller 210 may also monitor the desaturation timer $t_S$ at block S408. The controller 210 controls the image display device 140 according to an event detecting algorithm 800, and displays activated parameters according to display settings of screen information template setting algorithm 500 in block S414.

In block S416, the controller 210 determines if an algorithmic variable (s) is equal to 2. The algorithmic variable (s) indicates a status of a procedure (e.g. an intubation procedure) as determined from information provided by the continuous monitoring of the proximity sensor 114, the oxygen sensor 116, the anesthesia machine 118, the first position sensor 212, the second position sensor 216, the force sensor 218, and the optical imaging device 260. Where the algorithmic variable (s) is not equal to 2, the controller 210 monitors the sensors according to the monitoring sequence in block S412. Optionally, the controller 210 can set the monitoring sequence according to a priority of parameters related to the data obtained from the proximity sensor 114, the oxygen sensor 116, the anesthesia machine 118, the first position sensor 212, the second position sensor 216, the force sensor 218, and the optical imaging device 260 in block S418. On the other hand, if the algorithmic variable (s) is equal to 2, the method of operating an image display device 400 ends.

Figure 5:
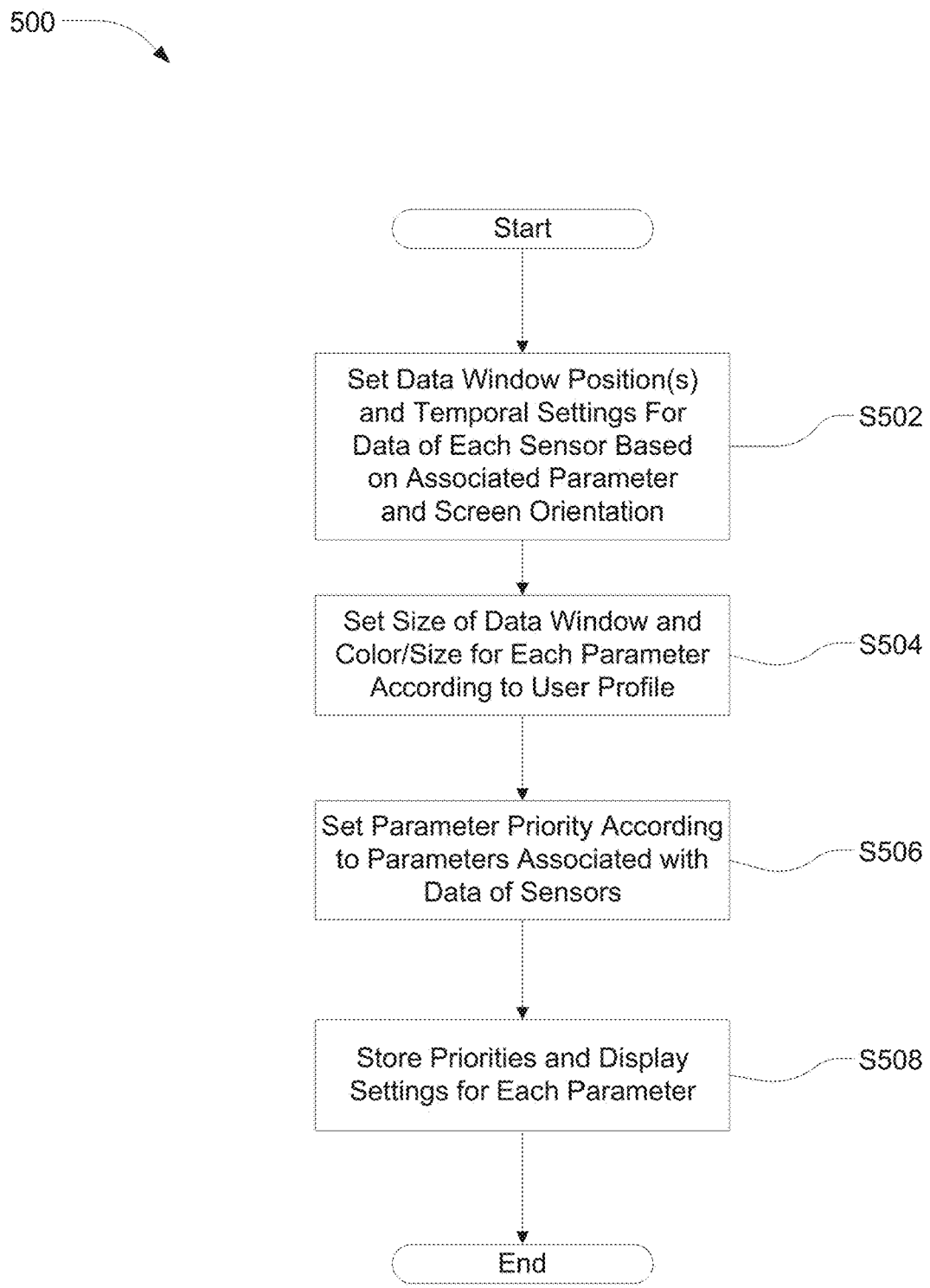
FIG. 5 is a flowchart illustrating a method of setting a screen information template for an image display device, according to an aspect of the present disclosure.

FIG. 5 is a flowchart illustrating a method of setting a screen information template for an image display device 500, according to an aspect of the present disclosure. In block S502, the controller 210 determines a screen position and temporal settings for data of each sensor based on an associated parameter and the orientation the screen 208. As described in more detail with reference to FIGS. 7A-D, positions of parameters are determined by the type of data, and the criticality of the operator having knowledge of the value of the parameter as to the procedure being performed. The temporal settings for each parameter may include a length of time that a particular parameter is displayed on the screen 208, or a frequency for which the parameter is repeatedly displayed (e.g. flashed) on the screen 208.

According to an aspect of the present disclosure, prior to setting the data window position(s), the controller 210 may estimate a field of view corresponding to an estimated field of view (EFOV) of an operator, based on an orientation of the image display device 140. The controller 210 may estimate the EFOV according to an orientation determined in S410, and/or data from the first position sensor 212 and the second position sensor 216 to determine a position of the screen 208 relative to an operator and the patient 102. Accordingly, the controller 210 may utilize the EFOV to determine an optimal location for a data window(s), for example where the screen 208 is not centered relative to a mouth of the patient 102.

The image display device 140 uses the entire screen for video imaging, and can be operative both in a portrait or landscape orientation. As discussed in more detail with respect to FIGS. 7A, B, and D, the same single fixed data window location can be used to display different parameters. Alternatively, each parameter may be assigned to a respective data window that may periodically cover part of a streaming video in a respective fixed position on the screen 208.

In block S506, the controller 210 sets a size for a data window and a color size for each parameter according to the user profile. In block S508, the controller 210 sets priorities for the parameters according to a determination of a criticality each parameter associated with each sensor, which may be based on a preprogramed analysis. According to an aspect of the present disclosure, the priority of a parameter may determine the order in which the parameter is displayed on the screen 208 of the image display device 140 and/or the monitoring sequence.

In block S510, the controller 210 stores the priorities and display settings for each parameter. Based on the stored priorities and display settings, the controller 210 may schedule different messages either placing multiple display windows, multiple pieces of information in each display window, or sequencing display windows. A display time and interval, i.e. temporal setting for each window, may be allocated according to interval settings of a parameter displayed in the display window. The controller 210 may remove messages when conditions sensed by an array of sensors (110, 114, 116, 216, 218, 260), indicate information associated with a parameter of a display window is no longer relevant.

Figure 6:
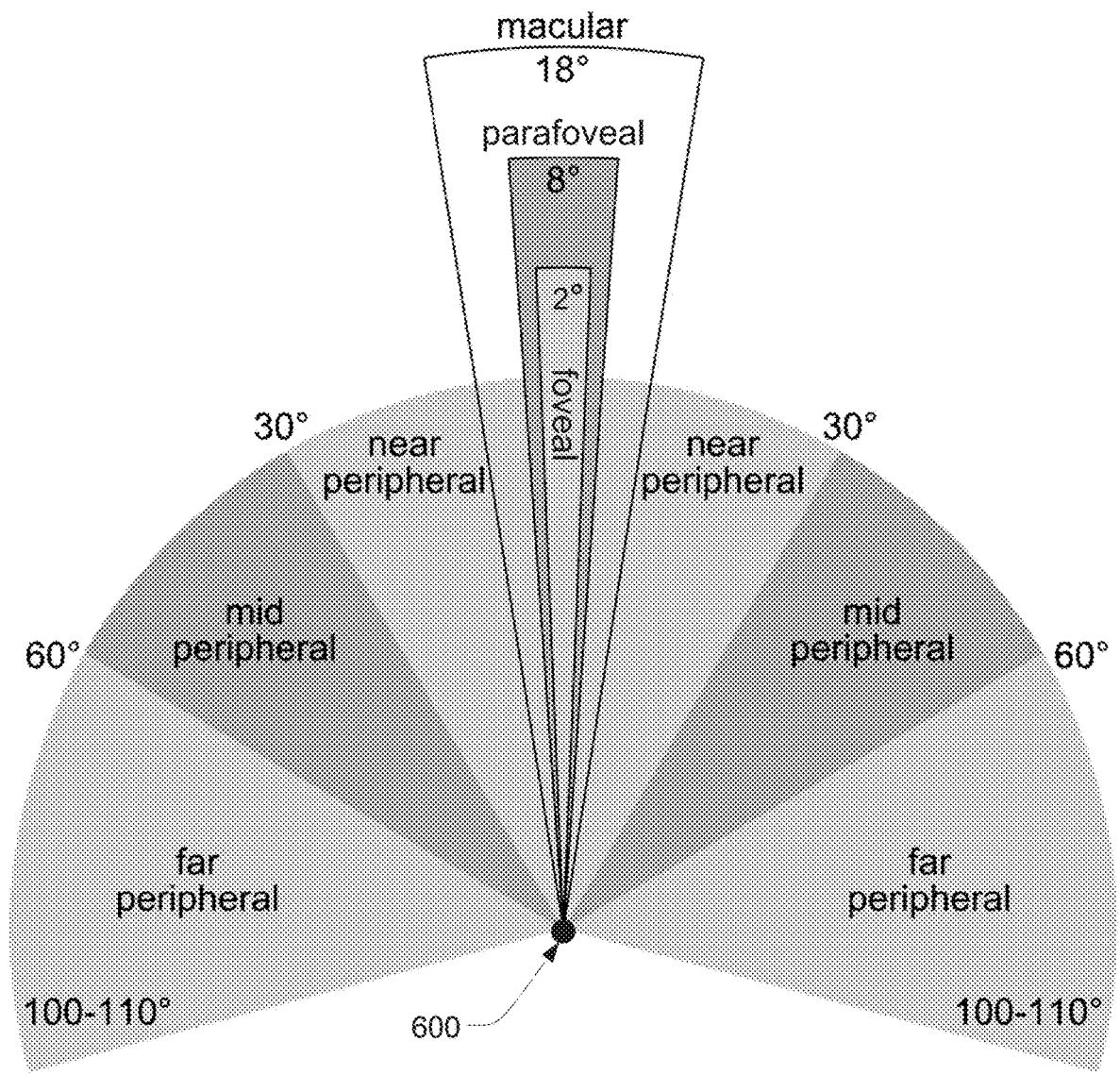
FIG. 6 illustrates a 2D representation of a 3D conical field of view of a human eye.

FIG. 6 illustrates 2D representation of a 3D conical field of view (FOV) of a human eye. A position of the eye corresponds to a first location 600. As illustrated in FIG. 6, a parafoveal vision is generally considered to be about 8°. The parafoveal vision corresponds to an intermediate form of vision represented by a ring-shaped region surrounding fovea vision of a human eye. Information being read within 2° of a point of fixation (POF) is processed in a foveal vision, while information up to 5° from the point of fixation benefits from parafoveal preview. When a character or a word is previewed in parafovea vision before fixation, processing time by a brain may be shorter (for example by 30-40 ms) than if the character or word had not been previewed.

Figure 7A:
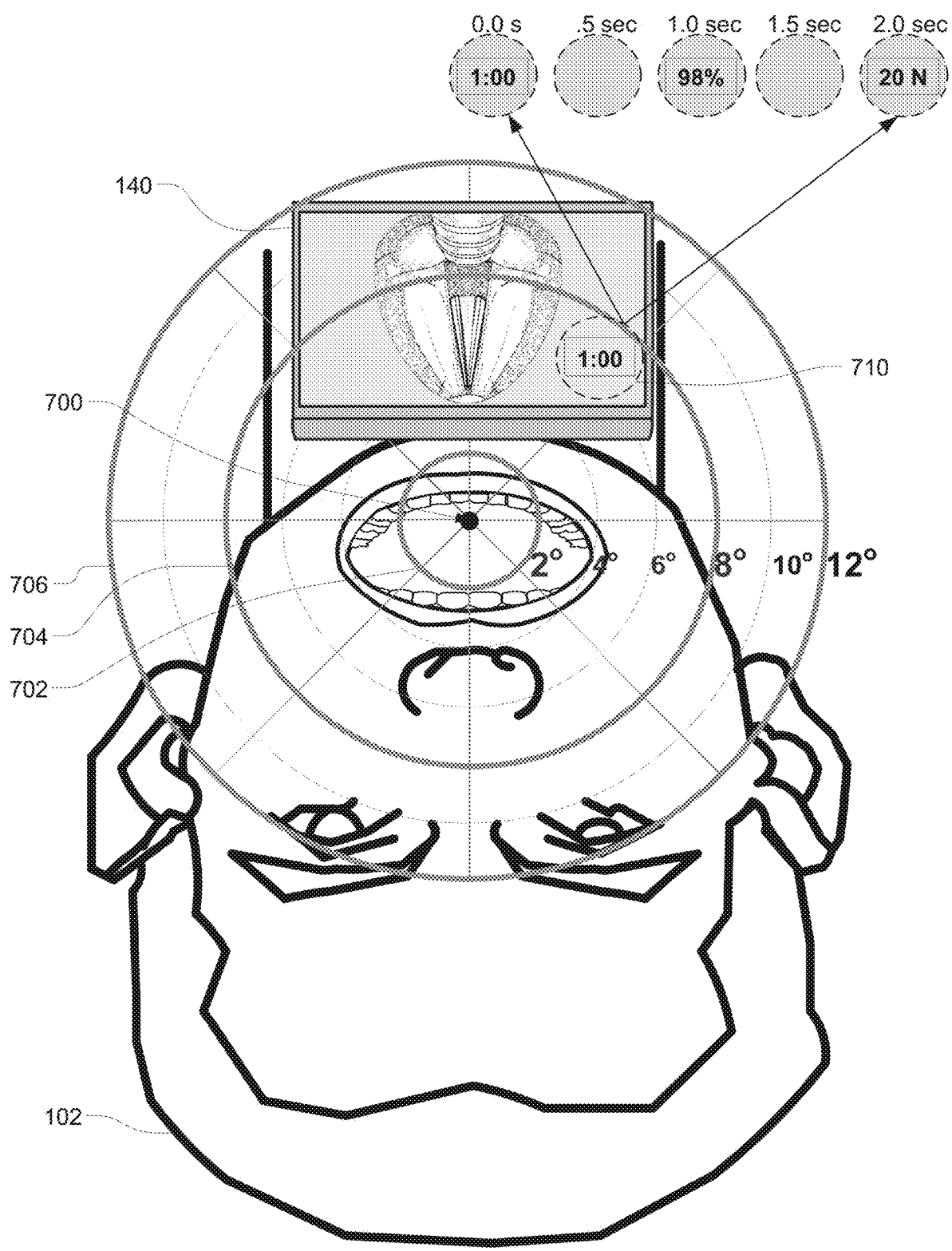
FIG. 7A illustrates a field of view of an operator during a medical procedure with an image display device in a first position, according to an aspect of the present disclosure.
Figure 7B:
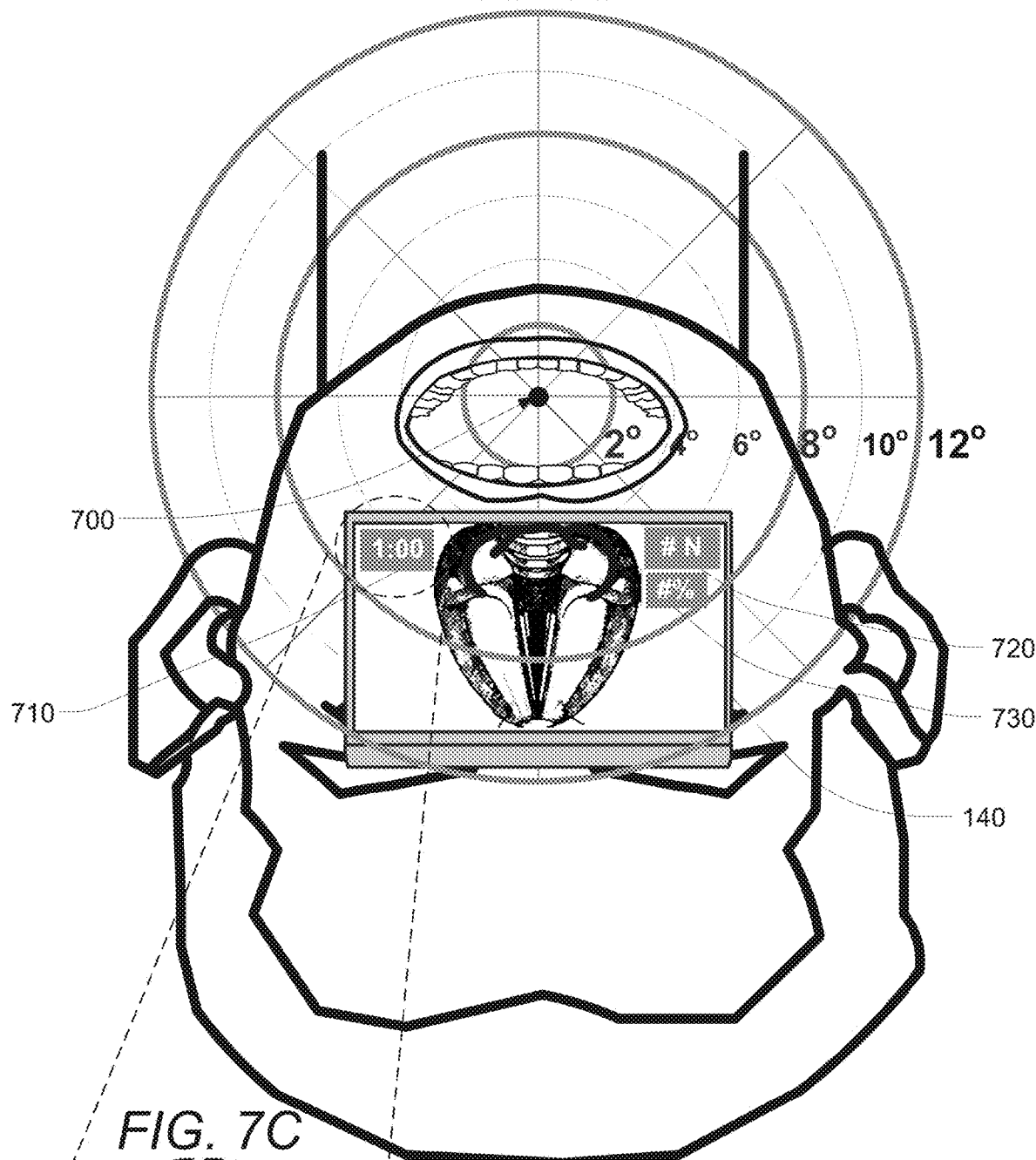
FIG. 7B illustrates a field of view of an operator during a medical procedure with an image display device in a second position, according to an aspect of the present disclosure.
Figure 7C:
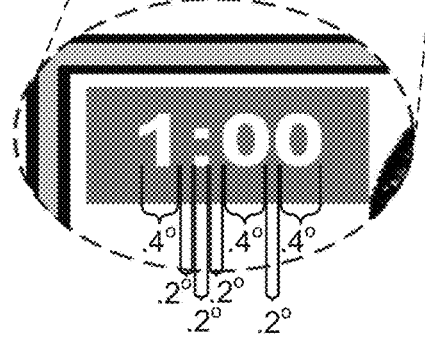
FIG. 7C illustrates an enlarged portion of FIG. 7B.
Figure 7D:
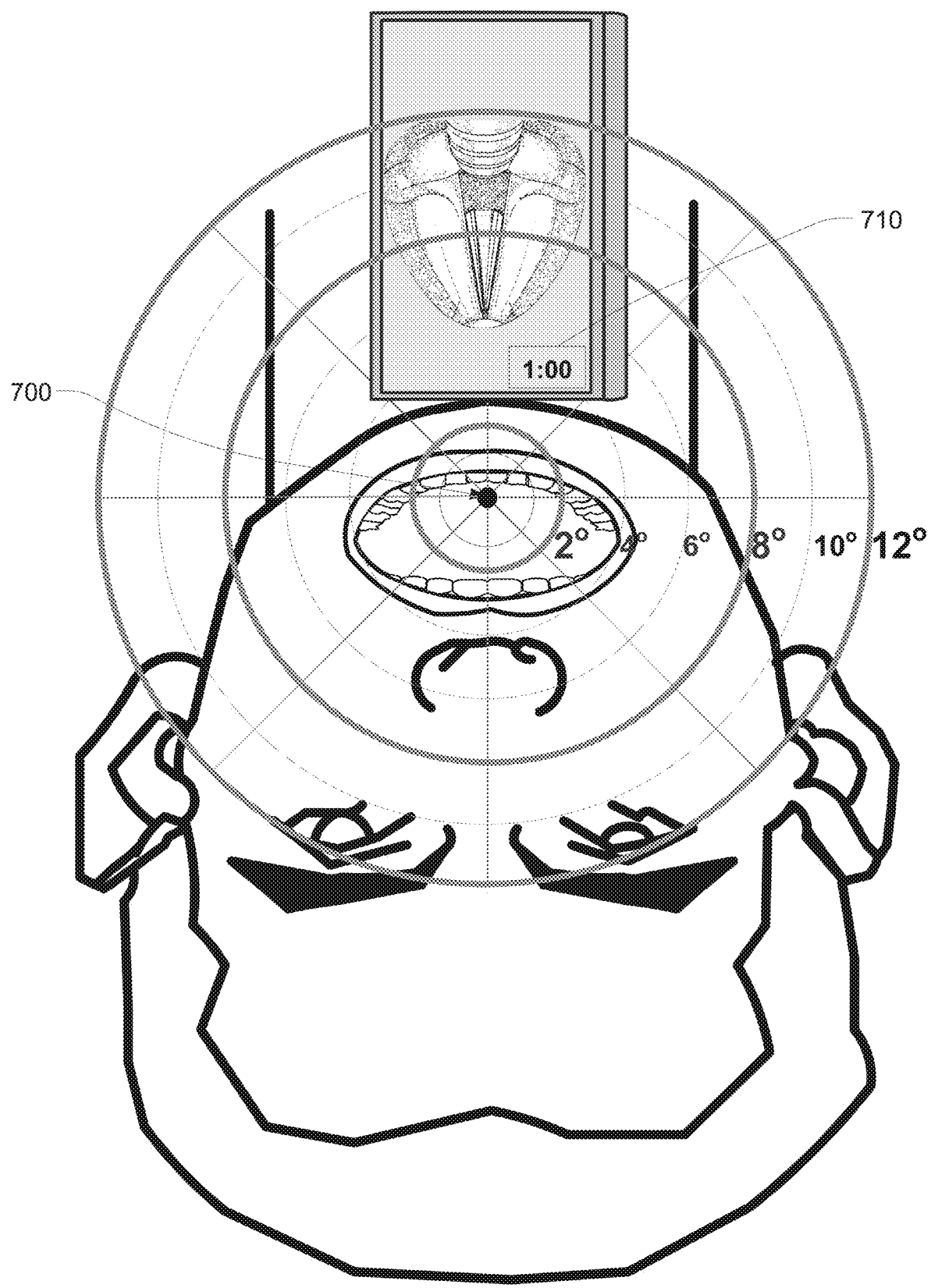
FIG. 7D illustrates a field of view of an operator during a medical procedure with an image display device in a third position, according to an aspect of the present disclosure.

FIG. 7A illustrates a field of view of an operator—FOV 706—(e.g. a visual FOV of a clinician, and more specifically a visual FOV of the second clinician of FIGS. 1A and 1B) during a medical procedure with the image display device 140 in a first position, according to an aspect of the present disclosure. FIG. 7B illustrates a field of view of an operator—FOV 706—during a medical procedure with the image display device 140 in a second position, according to an aspect of the present disclosure. FIG. 7C illustrates an enlarged portion of FIG. 7B, and specifically shows a relative size of characters on a screen with respect to the FOV 706 illustrated in FIG. 7B. FIG. 7D illustrates a field of view of an operator—FOV 706—during a medical procedure with the image display device 140 in a third position (i.e. a portrait orientation), according to an aspect of the present disclosure. It will be appreciated that FIGS. 7A-D are not drawn to scale and are general representations of an exemplary FOV 706 for an operator, and do not specifically correspond to the values for areas within a FOV discussed herein.

The FOV 706 of an operator performing a medical procedure, for example an intubation, may be focused on a lower head region of the patient 102, which may be roughly 10-12 cm in diameter, at a working distance from the operator of an arm's length of approximately 50 cm. A visual field about a point of fixation for the FOV 706 corresponding to the above working distance and diameter may be approximately 12°. An outer radial portion of the FOV 706 of an operator, as illustrated in FIGS. 7A, B, and D, surrounds a parafoveal FOV 704, which is concentric to a foveal FOV 702. It will be appreciated that the parafoveal FOV 704 and foveal FOV 702 illustrated in FIGS. 7A, B, and D, correspond to the 8° parafoveal vision, and the 2° foveal vision illustrated in FIG. 6.

In order for the image on the image display device 140 to be within an operator's parafoveal FOV 704, e.g. within 8°-10° about a second location 700 at or near a mouth region of the patient 102, a size of the screen 208 of the image display device 140 may be approximately 3 inches×2 inches. With this size, the screen 208 may extend over 8° of an operator's FOV focused on the screen 208 for the working distance previously discussed. Accordingly, parameters displayed on the screen 208 are in the parafoveal FOV 704 of an operator so as to be previewed prior an operator fixating on a given parameter or other image on the screen 208.

A size of a character displayed on the screen 208 is such that the character is instantly recognizable at the working distance, similar to a print size of characters in a headline. It will be understood that a font of characters of a standard headline print size may occupy an area in a range corresponding to 0.4°-0.8° of an operator's FOV, as illustrated in FIG. 7C. The controller 210 of the image display device 140 may arrange letter spacing so as to not be overly crowded, and preferably greater than 0.2°-0.3° of and operator's FOV. According an aspect of the present disclosure, a three digit display with a colon separating minutes and seconds is displayed on the image display device 140 over an area occupying between 1.5° to 2.5° of an operator's 8° parafoveal FOV, as illustrated in FIG. 7C.

During a medical procedure, such as a procedure including an intubation of the patient 102, an operator may deploy the screen 208 comfortably within the operator's line of sight. The screen 208 of the image display device 140 may preferably be positioned in a line of sight of an operator performing an intubation to be within an FOV of the operator that is concentrated on a lower part of the face and jaw of the patient 102. As illustrated in FIGS. 7A-C, the screen 208 can be either above or below the mouth of the patient 102, and can be orientated according to a portrait or landscape orientation.

As illustrated in FIG. 7A, the controller 210 may display parameters in a display window 710 in a single location close to the mouth of the patient 102. As previously discussed, the controller 210 may cycle through the parameters, flashing each parameter over a predetermined interval of time. FIG. 7A illustrates an example of a cycle in which time, oxygen saturation level, and force are displayed on the image display device 140. Specifically, at time 0.0 seconds—a time which may correspond to an elapsed time since an oxygen mask was removed or since an intubation device was brought within a view of a mouth of the patient 102—may be displayed for 0.5 seconds.

At 0.5 seconds, the display window 710 may cycle from displaying the time to displaying a portion of an image which was covered by the data in the display window from 0.0 to 0.5 seconds, and therefore not include any parameter representing data from any source such as a sensor. This display of the video image, for example from the first optical imaging device 260, in the location of the display window 710, may continue for 0.5 seconds. Following the display of the video image, at 1.0 seconds, an oxygen saturation level is displayed in the display window 710. After the oxygen saturation level is displayed for 0.5 seconds, the controller 210 may cycle from displaying the oxygen saturation parameter in the display window, to again displaying a portion of the video image which was covered by the data in the display window 710 from 1.0 to 1.5 seconds, and therefore not include any parameter representing data from any source such as a sensor. The display of the video image in the location of the display window 710 may continue for 0.5 seconds, and at 2.0 seconds, a detected force may be displayed in the display window 710. Accordingly, the controller 210 may operate the image display device 140 to cycle through displays of parameters, separated by displays of a portion of a video image that would be covered by the display window 710 that displays the parameters during the cycle.

As illustrated in FIG. 7B, according to another aspect of the present disclosure the controller 210 may display each parameter in a different display window (710, 720, 730) at a corner or edge of the screen 208, close to a mouth region of the patient 102. The display windows (710, 720, 730) correspond to positions for activated parameters assigned as a result of the controller 210 operating the image display device 140 according to the Screen Information Template Setting algorithm 500. The display windows (710, 720, 730) enclose respective parameters expressed as text or digits which are large enough to be easily recognized and contrasted to a single pantone background. Each display window occupies an area corresponding to less than 2° of the FOV for the working distance as discussed herein. According to an aspect of the present disclosure, the characters (text or digits) may be larger than 0.2° of the FOV, and preferably in a range of 0.4° to 0.8°, and separated over spaces corresponding to 0.2° of the FOV as illustrated in FIG. 7C.

The image display device 140 preferably shows a window as represented by the screen 208, which includes critical real time procedure (e.g. intubation) data on a single pantone rectangular background as opposed to a video background cluttered with tissue image. Thus, the screen 208 may display critical real time intubation data in a similar manner as a highway signage to provide easily read information as well as warning information.

FIGS. 7A-D further illustrate display settings for the image display device 140, according to an aspect of the present disclosure. A color of a background, contrast of an image displayed on the screen 208, color of a display window 710, and the text within the display window 710 can be changed. The change in colors, contrasts, data types of parameters displayed within the display windows (710, 720, 730), and the size of the display windows (710, 720, 730), may be set according to the controller 210 operating according to the screen information template setting algorithm 500.

Colors, size, data type, and other aspects of respective visual presentations of parameters can change over the course of a procedure according to the display settings provided through screen information template setting algorithm 500 as discussed herein. According to an aspect of the present disclosure, preferable color contrasted combinations may include a display window with black characters on a pale background, for example, yellow, similar to highway warning; blue letters on white background; or a display window with white characters on a green background similar to highway signs. Further, display windows (710, 720, 730) may present activated parameters based on trigger events, and the display windows (710, 720, 730) may be flashed in a repeating pattern such that a given display window and parameter therein, is present for at least 0.5 seconds to ensure that the parameter can be recognized properly. The pattern may include flashing the given display window a minimum number of times within an interval, allowing an operator to see a portion of an image on the screen 208 which is a part of the image transmitted by the first optical imaging device 260 where the given display window is being flashed.

Figure 8:
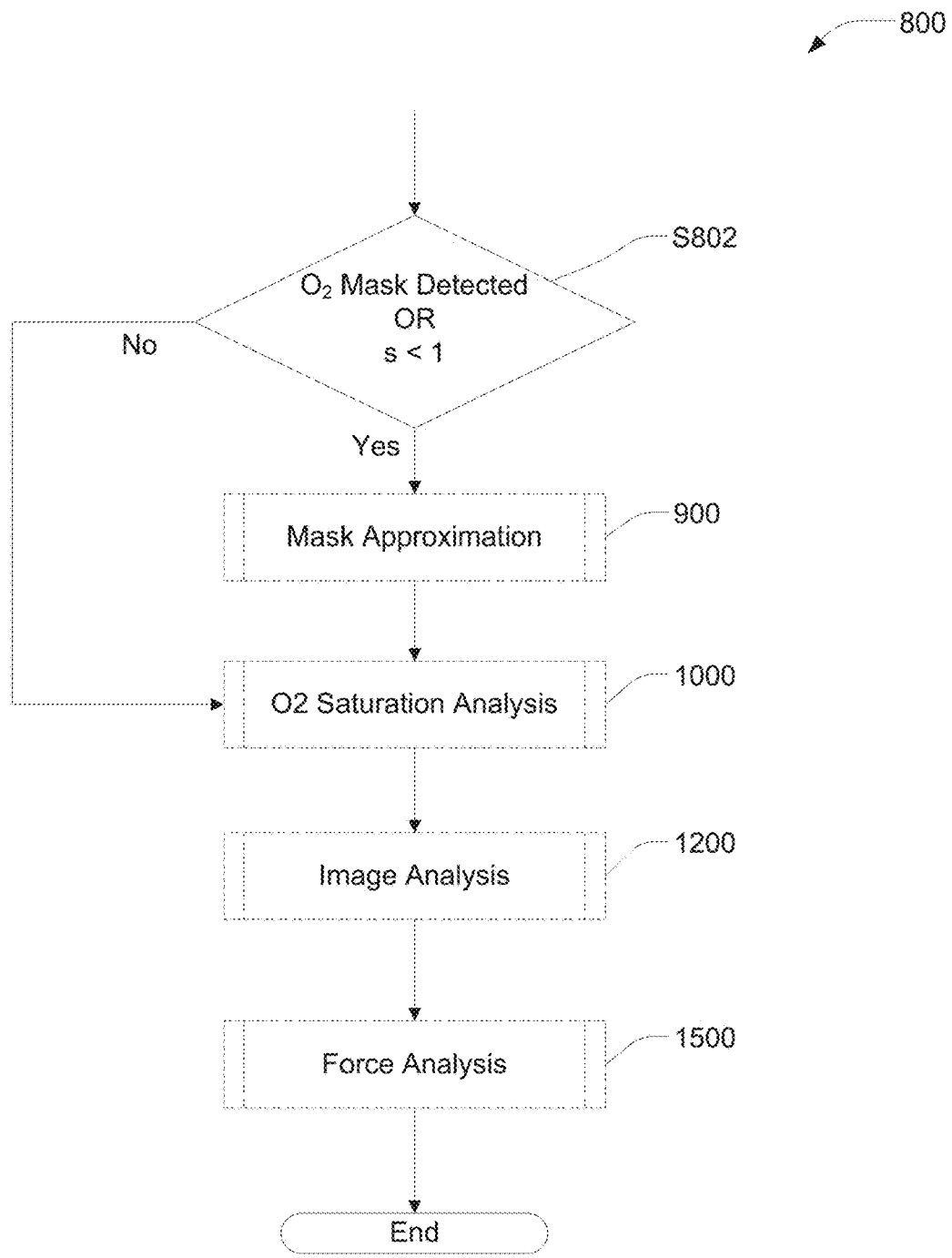
FIG. 8 is a flowchart illustrating a method for event detecting, according to an aspect of the present disclosure.

FIG. 8 is a flowchart illustrating a method for event detecting 800, according to an aspect of the present disclosure. In block S802, the controller 210 determines if the mask has been detected. If the mask 110 has been detected, the controller 210 may operate the image display device 140 according to a mask approximation algorithm 900. If the mask 110 has not been detected, the controller 210 may operate the image display device 140 according to an oxygen saturation algorithm 1000, an image analysis algorithm 1200, and/or a force analysis algorithm 1500. It will be understood that any of one the mask approximation algorithm 900, the oxygen saturation algorithm 1000, the image analysis algorithm 1200, and the force analysis algorithm 1500 may be performed independent of the other algorithms of FIG. 8. Accordingly, all, some, or even none of the algorithms of FIG. 8 may be performed for the method of operating a video display 400. Each of the sensors (114, 116, 212, 216, 218, 260) are simultaneously and continuously operated, and sensor readings are available for display at all times and when necessary.

Figure 9:
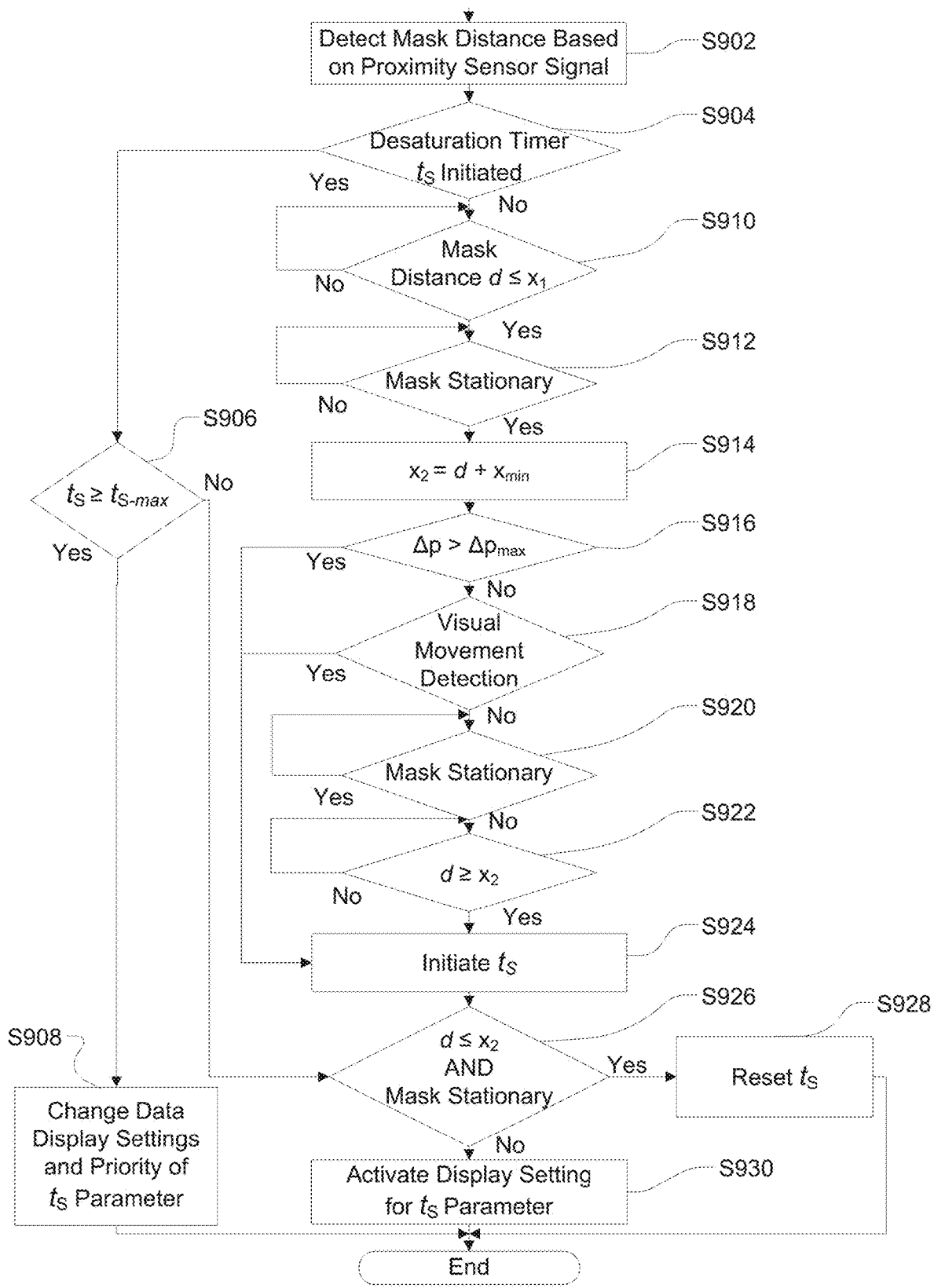
FIG. 9 is an algorithmic flowchart illustrating a method of approximating a position of a mask, according to an aspect of the present disclosure.

FIG. 9 is an algorithmic flowchart illustrating a method of approximating a position of a mask 900 during a procedure, according to an aspect of the present disclosure. In block S902, the controller 210 detects the mask 110 based on a signal from the proximity sensor 114. In block S904, the controller 210 determines if an oxygen desaturation timer $t_S$ is initiated. The oxygen desaturation timer $t_S$ indicates a time for which oxygen is not being provided through the mask 110 to the patient 102. According to an aspect of the present disclosure, the desaturation timer $t_S$ can be implemented in a standalone device (not shown), such as a discrete standalone image display device, or be integrated with anesthesia machine 118. The image display device 140 can optionally wirelessly receive desaturation time for display which can otherwise be displayed on the standalone device or the anesthesia machine 118. Where the oxygen desaturation timer $t_S$ has been initiated, the controller 210 determines if the value of the oxygen desaturation timer $t_S$ is greater than or equal to an oxygen desaturation maximum time $t_{S-max}$, which may correspond to an elapsed time the patient has not been provided with oxygen (e.g. a time since a mask was removed from the patient).

Where the value of the oxygen desaturation timer $t_S$ is greater than or equal to the oxygen desaturation maximum time $t_{S-max}$, the controller 210 changes data display settings and priority of the oxygen desaturation timer $t_S$ parameter. Accordingly, the parameter for the oxygen desaturation timer $t_S$ may change from a numeral or time value, to a text value, such as a warning text, or to a numeral or time value and a text value. Further, the priority of the oxygen desaturation timer $t_S$ may be changed to be higher than another parameter, for example a parameter associated with the force sensors 218. Accordingly, the parameter for the oxygen desaturation timer $t_S$ may be displayed first and the most often based on a respective priority, as a result of the value of the timer $t_S$ being more than the oxygen desaturation maximum time $t_{S-max}$.

In a situation in which the controller 210 determines the oxygen desaturation timer $t_S$ has not been initiated in block S904, the controller 210 determines if a distance d between the proximity sensor 114 and the magnet 112 is less than or equal to a first distance threshold $x_1$ in block S910. This will indicate if the mask 110 is close enough to the proximity sensors 114 for the mask 110 to be considered as being close to or on the patient 102. The controller 210 repeats an analysis according to block S910 until the mask distance d is less than or equal to the first distance threshold $x_1$. In block S912, with the mask 110 at a distance d less than or equal to the first distance threshold $x_1$, the controller 210 determines, based on the signals from the proximity sensors 114, or a reading from the anesthesia machine 118 which communicates with the proximity sensors 114, if the mask 110 is stationary.

The process in block S912 provides an indication that the mask 110 has been fixed onto a patient 102 so that the controller 210 can determine a baseline distance from which to compare to determine if the mask 110 has been removed from the patient 102. As such, the controller 210 sets a second distance threshold $x_2$ to the current mask distance d plus a minimum distance $x_{min}$ in block S914.

In block 916, the controller 210 may communicate with the anesthesia machine 118 do determine if the anesthesia machine has detected a drop in pressure from the mask 110 indicated it has been removed from the patient 102. In particular, the mask 110 may include a pressure sensor or the anesthesia machine 118 may include a pressure sensor which registers a reduction in pressure in an oxygen supply line when the mask 110 is removed from the patient (since there is reduced resistance to oxygen flow because the flow of oxygen is not impeded by the patient 102). If there is no pressure drop/change in pressure greater than a maximum change pressure threshold $\Delta p_{max}$, the controller will determine if an auxiliary visual recording device/optical imaging device (not shown) has registered a removal of the mask 110 from the patient. If either of the conditions is determined to have been met in block S916 or block S918, the controller 210 will initiate the oxygen desaturation timer $t_S$ in block S924.

If the oxygen desaturation timer $t_S$ is not initiated with block S916 or block S918, the controller 210 checks to see if the mask 110 is being moved from the patient 102 in block S920. Where the mask 110 has been moved from the patient 102, the controller 210 determines if the movement is far enough from the patient in block S922 to correspond to a situation in which the mask 110 is being removed for an intubation procedure to follow. The second distance threshold $x_2$ is set to avoid initiating the oxygen desaturation timer $t_S$ in block S922 where the mask 110 has only been slightly adjusted and not fully removed from patient 102. The controller 210 will initiate the oxygen desaturation timer $t_S$ in block S924 when it is determined the mask distance d is greater than the second distance threshold $x_2$.

In block S926, the controller 210 determines if the mask 110 has been put back on the patient 102 and is stationary by comparing a signal from the proximity sensor to the second distance threshold $x_2$. Where the mask 110 has been put back on the patient 102, in block S928, the controller 210 resets the oxygen desaturation timer $t_S$ and sets the first algorithmic variable (i) to zero, indicating that an intubation procedure will not be occurring at the current time. On the other hand, if the controller 210 determines the mask 110 is removed from the patient 102, the display settings for the parameter for the oxygen desaturation timer $t_S$ for the current time $T_1$ are activated. Accordingly, with the proximity sensor(s) 114, the controller 210 can determine events that correspond to a pre-oxygenation time and a time at which the mask 110 is removed and desaturation begins have occurred.

According to an aspect of the present disclosure, a detection of a removal of the mask 110 from the patient 102 may occur through detecting the movement of the mask 110 via the proximity sensor 116, detecting a drop in pressure from the mask 110, or through an observation through an optical imaging device that is, for example, mounted on the anesthesia machine 118 or another device. Further, any of these processes for detecting the removal of the mask 110 may be implemented directly by the image display device 140 or the anesthesia device 118. The information related to the removal of the mask 110, e.g. the start of the oxygen desaturation timer $t_S$, may be displayed on either of the image display device 140 or a monitor/display device of the anesthesia machine 118.

The image display device 140 or the anesthesia machine 118 may be in communication with the sensor(s) which detect events from which the removal of the mask 110 can be determined (e.g. the distance, pressure drop, visual recognition), and transmit data indicating the removal of the mask 110 to the other of the image display device 140 and the anesthesia machine 118 via various modes of communication there between (e.g. Bluetooth, Wi-Fi, NFC). Further, either of the image display device 140 and the anesthesia machine 118 which communicates with the sensors can initiate the oxygen desaturation timer $t_S$ and transmit the value of the oxygen desaturation timer $t_S$ to the other of the image display device 140 and the anesthesia machine 118. For example, the anesthesia machine 118 may communicate with the proximity sensor 116, determine the drop in pressure in the mask 110, initiate the oxygen desaturation timer $t_S$, and send the value of the oxygen desaturation timer $t_S$ to the image display device 140.

According to another aspect of the present disclosure, either of the image display device 140 or anesthesia machine can register the removal of the mask 110 upon receiving data from the other of the image display device 140 and the anesthesia machine 118, then initiate the oxygen desaturation timer $t_S$, and then, transmit the value of the oxygen desaturation timer $t_S$ back to the device which registered the removal of the mask 110. For example, the image display device 140 may communicate with the proximity sensor 116 and send a reading of the proximity sensor 116 to the anesthesia machine 118, which then determines the mask 110 has been removed, initiates the oxygen desaturation timer $t_S$, and sends the value of the oxygen desaturation timer $t_S$ to the image display device 140. As the anesthesia machine 118 communicates the value of oxygen desaturation timer $t_S$, the anesthesia machine 118 could possibly be displaying oxygen desaturation timer $t_S$ on a monitor thereof. It will be understood that the above process could be performed with the image display device 140 and anesthesia machine 118 switching roles.

Figure 10:
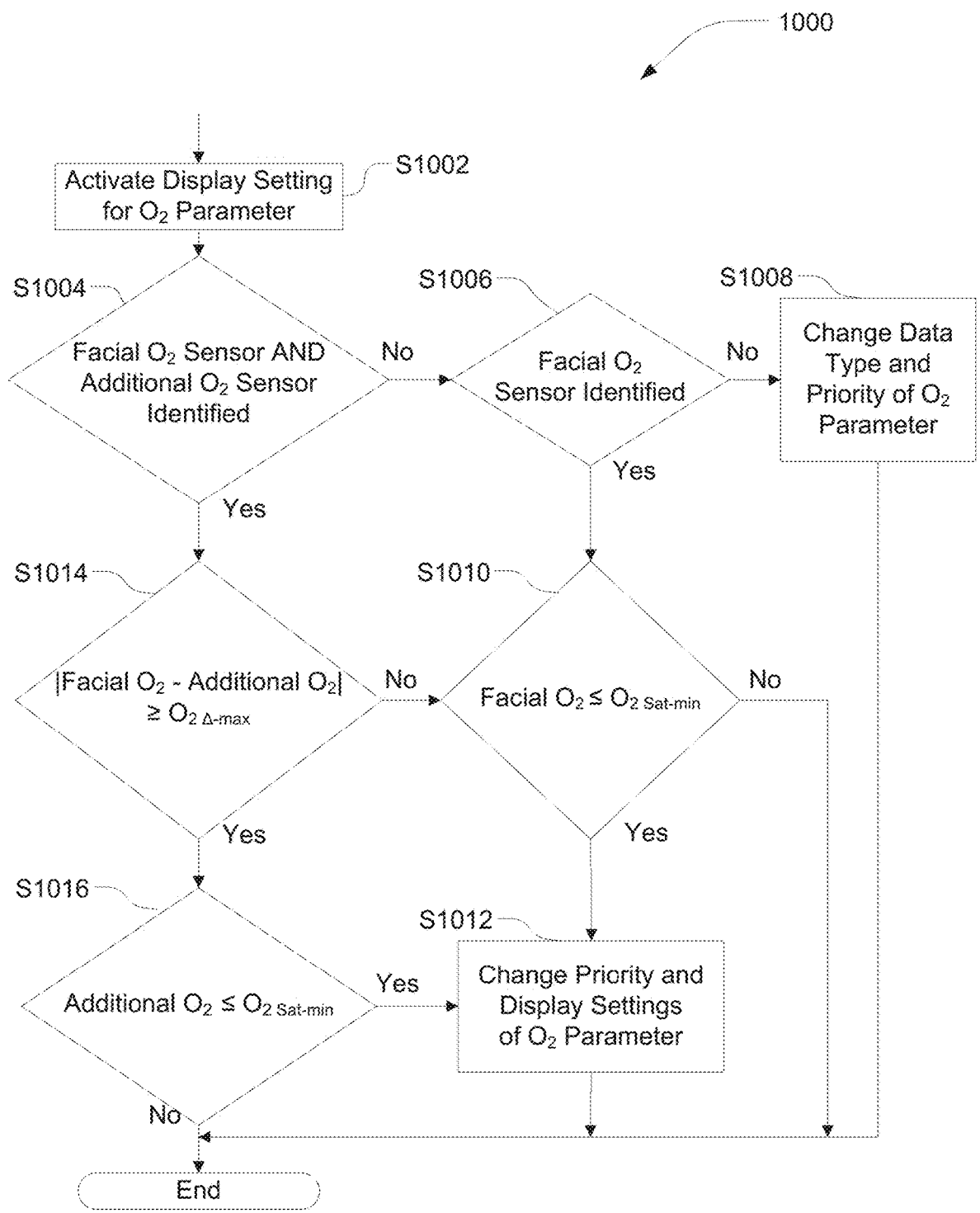
FIG. 10 is an algorithmic flowchart illustrating a method of analyzing an oxygen saturation level, according to an aspect of the present disclosure.

FIG. 10 is an algorithmic flowchart illustrating a method of analyzing an oxygen saturation level 1000, according to an aspect of the present disclosure. In block S1002, the controller 210 activates display setting for an oxygen ($O_2$) saturation parameter. If multiple $SpO_2$ sensors (hereafter referred to as "oxygen sensor", "oxygen sensors", "$O_2$ sensor", or "$O_2$ sensors") are available, then depending on a user profile and/or the controller 210 operating the image display device 140 according to the screen information template setting algorithm 500, the controller 210 may present, for example an anesthesia machine reading parameter as well as a separate facial $O_2$ parameter in the same display window. In addition, as a reading of the facial $O_2$ sensor drops, the controller 210 may change colors of the facial $O_2$ parameter transition from white on green, to black on yellow, for example.

In block S1004, the controller determines if a facial $O_2$ sensor, such as any of the oxygen sensors 116 in FIG. 1A, and any additional $O_2$ sensors have been identified. The additional sensor could be an additional oxygen sensor attached to the patient, a pulse oximeter attached to a finger of the patient 102, or another oxygen sensor connected to the anesthesia machine 118. Where a combination of a facial $O_2$ sensor and an additional $O_2$ sensor have not been identified, the controller 210 determines if a facial $O_2$ sensor has been identified in block S1008.

If a facial $O_2$ sensor has not been identified, corresponding to a situation in which no oxygen sensors have been identified by the controller 210, the data type and the priority of the $O_2$ saturation parameter is changed in block S1008. This corresponds to a situation in which the oxygen saturation of the patient 102 cannot be determined, and may require a procedure to be stopped. Accordingly, the controller 210 may change the priority of the $O_2$ saturation parameter to ensure that an operator is aware that an oxygen saturation level is not available.

If a facial $O_2$ sensor is identified in block S1006, or it is determined that a difference between detected oxygen saturation levels by the facial $O_2$ sensor and any additional $O_2$ sensor is not greater than or equal to a maximum deviation $O_{2\Delta\text{-}max}$ in block S1014, the controller determines if an oxygen saturation detected by the facial $O_2$ sensor is less than or equal to a threshold minimum saturation level $O_{2\ Sat\text{-}min}$ in block S1010. Accordingly, a benefit of displaying an oxygen saturation level that does not suffer from lag because an oxygen sensor is positioned on a forehead of a patient can be obtained. If the detected saturation is not above the threshold, then the method of analyzing an oxygen saturation level 1000 is completed. On the other hand if the detected saturation is above the threshold, the controller 210 changes the priority and display settings of the $O_2$ saturation parameter.

A change to the display settings of any parameter may include a change to the size, color, and temporal settings of the parameter. For example, whereas the display settings for the $O_2$ saturation parameter may have previously included black digits in a yellow display window that did not flash, a new display setting for the $O_2$ saturation parameter may include a red display window and white digits that flash according to a predetermined frequency.

Where it is determined in block S1014 that the absolute value of the deviating between a reading from the facial $O_2$ sensor is greater than or equal to the maximum deviation $O_{2\Delta\text{-}max}$, which may indicate the facial $O_2$ sensor is not providing an accurate reading, the controller 210 can determine if an oxygen saturation detected by the additional $O_2$ sensor is less than or equal to the threshold minimum saturation level $O_{2\ Sat\text{-}min}$. Accordingly, displaying an erroneous reading of a facial $O_2$ sensor caused by interference from veinous pulsations when a patient is in a supine position can be avoided. Where it is the case that the oxygen saturation detected by the additional $O_2$ sensor is less than or equal to the threshold minimum saturation level $O_{2\ Sat-min}$, the controller 210 changes the priority and display settings of the $O_2$ parameter. Otherwise, the method of analyzing an oxygen saturation level 1000 ends.

Figure 11:
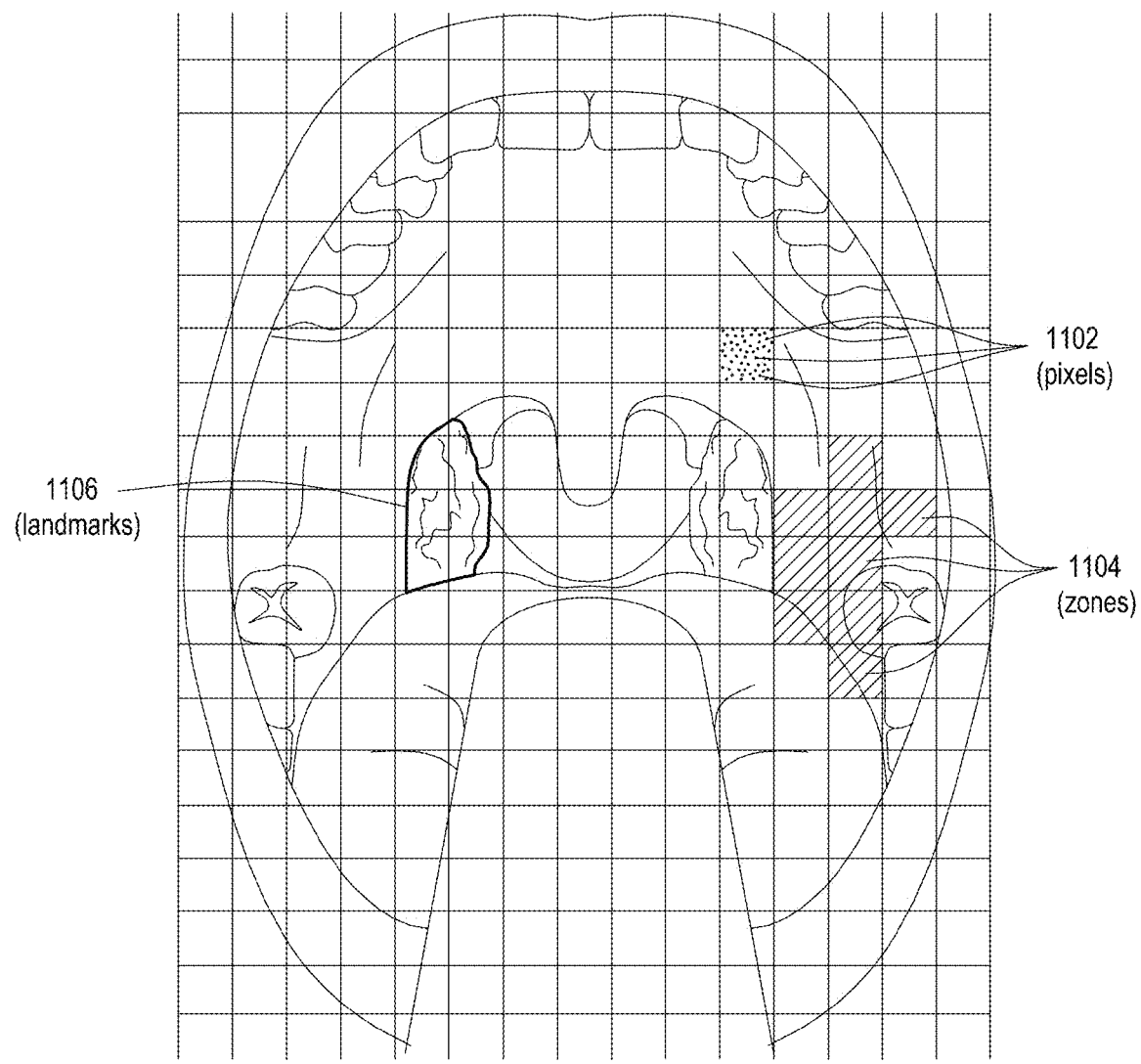
FIG. 11 illustrates a view from an optical imaging device divided into optical segments, according to an aspect of the present disclosure.

FIG. 11 illustrates a view from the optical imaging device 260 during a procedure, divided into optical segments (pixels and zones), according to an aspect of the present disclosure. In particular, FIG. 11 illustrates optical parameters by which an image from the first optical imaging device 260 can be segmented and evaluated by for the purposes of determining which parameters should be activated and, which image between multiple images sources may be displayed on the screen 208 of the image display device 140. The controller 210 may also do an image analysis according to landmark recognition.

According to an aspect of the present disclosure, the controller 210 may employ the first optical imaging device 260 as an event generation sensor in the sense that it determines a number of pixels that are predominantly red (e.g. a color corresponding to a first range within an optical spectrum) based on a signal strength in a red channel relative to other RGB channels. As will be explained in more detail with respect to FIG. 12, the controller 210 may apply threshold criteria to recognize events to trigger different responses that are expressed based on the display settings of the image display device 140. For example, the controller 210 may apply threshold criteria to the signal strength of the red channel to determine the intubation device 250 is being inserted into a mouth of the patient 102, and start and display a timer (intubation device timer $t_D$) associated with an act of inserting the intubation device 250. According to an aspect of the present disclosure, image processing by the controller 210 may include segmenting and classifying an image into red zones versus zones of a predominantly other color, and setting a criteria based on a size and number of red zones. Further, an image analysis employed by the controller 210 may be equivalent to classifying and segmenting an image between tissue and foreign objects to detect a foreign object, such as a stylet or intubation tube.

Figure 12:
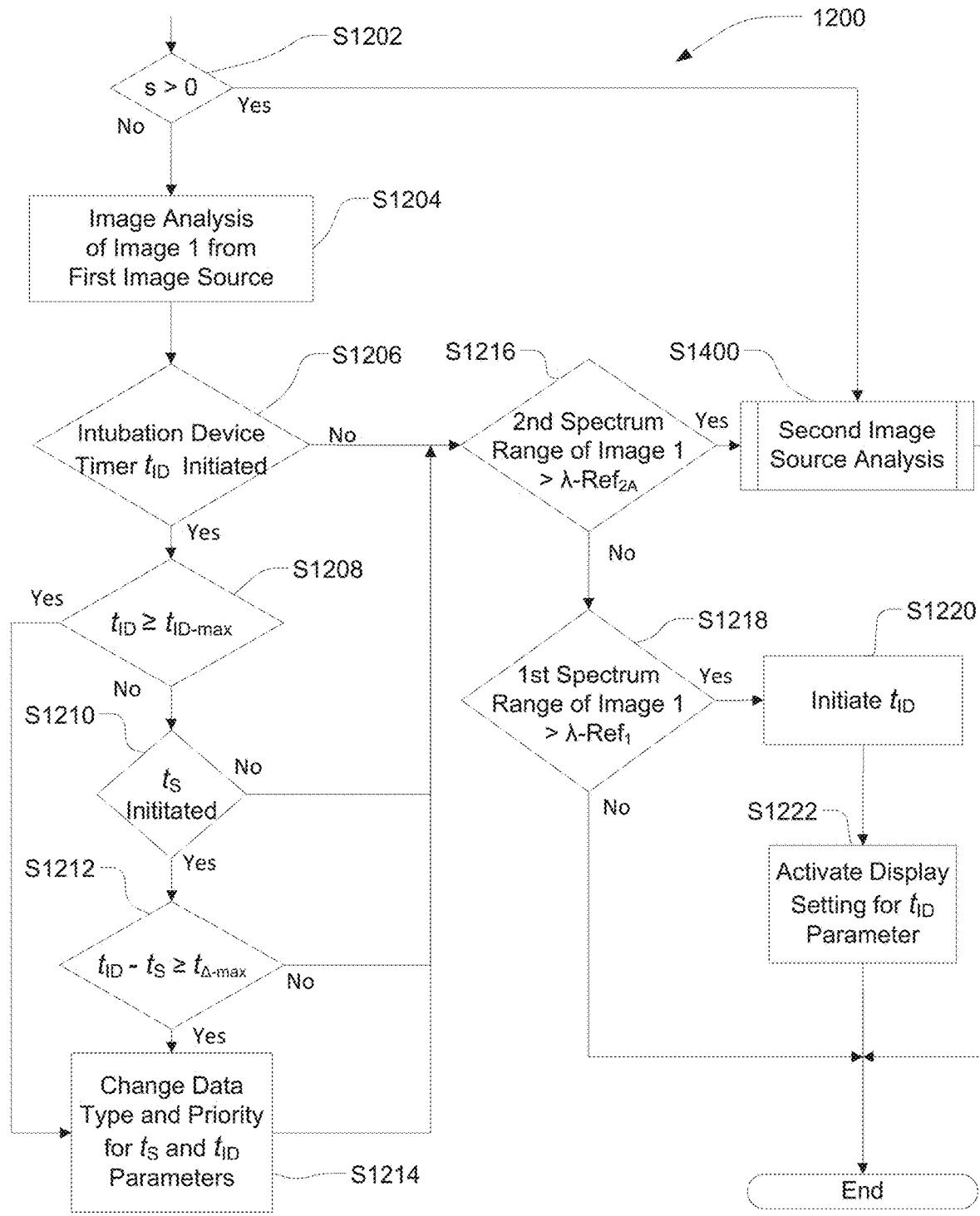
FIG. 12 is an algorithmic flowchart illustrating a method of analyzing an image obtained by an optical imaging device, according to an aspect of the present disclosure.

FIG. 12 is an algorithmic flowchart illustrating a method of analyzing an image obtained by an optical imaging device 1200, according to an aspect of the present disclosure. The foregoing discussion refers to the intubation device 250 illustrated in FIGS. 2 and 3. However, it will be appreciated that the image display device 140 may perform any of operations described herein, as provided in combination with different types of intubation devices generally represented in FIGS. 1A and 1B with the intubation device 150.

In block S1202, the controller 210 determines whether the algorithmic variable (s) is greater than zero. Where the algorithmic variable (s) is greater than zero, the controller 210 operates the image display device 140 according to a second image source analyzing algorithm 1400. This corresponds to a situation in which the controller 210 has previously analyzed the image from the first image source (e.g. the first optical imaging device), and determined that an image from a second image source (e.g. a stylet of the tube or coaxial arrangement of tube devices 170) is potentially ready to be viewed on the image display device 140 because the second image source has been inserted into the patient 102 and has an unobstructed view of the larynx or trachea of the patient 102. Otherwise, the controller 210 analyzes the image from the first optical imaging device 260 in block S1204. The controller 210 may perform a zone analysis, a pixel analysis by analyzing a signal for RGB color channels, and a landmark recognition analysis in block S1204.

In block S1206, the controller 210 determines if an intubation device timer $t_D$ is initiated. The intubation device timer $t_D$ indicates that an operator has begun to insert, for example the blade 258 of the laryngoscope provided by the intubation device 250, into a mouth of the patient 102. As will be described in more detail with respect to block S1218, the controller 210 determines from the image analysis in block S1204, whether the image 1 has a value for a 1st spectrum range that corresponds an open mouth of a person.

In block S1208, the controller 210 determines whether a value of the intubation device timer $t_D$, which was determined to be have been initiated in block S1206, is greater than or equal to a maximum value $t_{D-max}$, and thus indicates whether an operator has been trying to insert the intubation device 250 for too long. Thus the controller 210 can, independent of whether the oxygen desaturation timer $t_S$ has been initiated, determine if a specific process of an intubation procedure directly related to when the patient 102 will be able to safely receive an intubation tube is taking too long. Accordingly, if the controller 210 is unable to determine when the mask 110 has been removed, or for procedures in which the mask 110 is not detected and thus a removal thereof cannot indicate a beginning of a procedure, the controller 210 can obtain data and display a parameter that advises an operator how much time has elapsed since the intubation device 250 was brought into a position immediately before being inserted into the patient 102.

In block S1210, the controller 210 determines if the oxygen desaturation timer $t_S$ has been initiated. In block S1212, the controller 210 determines if a difference between values of the oxygen desaturation timer $t_S$ and intubation device timer $t_D$ is greater than or equal to a maximum timer difference $t_{\Delta-max}$. In the event the controller 210 determines the value of the intubation device timer $t_D$ is greater than or equal to the maximum value $t_{D-max}$ in block S1208, or a difference between values of the oxygen desaturation timer $t_S$ and intubation device timer $t_D$ is greater than or equal to a maximum timer difference $t_{\Delta-max}$ in block S1212 the controller 210 changes data types and priorities for oxygen desaturation timer $t_S$ and intubation device timer $t_D$ parameters.

In block S1216, the controller 210 determines if the value for a 2nd spectrum range of the image 1 from the first image source (e.g. the first optical imaging device 260) is greater than a 1st reference value for the second spectrum range $\lambda\text{-Ref}_{2A}$. The controller 210 operates the image display device 140 according to a second image source algorithm 1400 where the 2nd spectrum range of the image 1 is greater than the 1st reference value $\lambda\text{-Ref}_{2A}$ (i.e. reference value A of a set of reference values related to a wavelength corresponding to the 2nd spectrum range). Otherwise, the controller 210 determines a value of a 1st spectrum range in block S1218.

The 2nd reference value for the 2nd spectrum range $\lambda\text{-Ref}_{2A}$ is associated with a wavelength in an optical spectrum that corresponds to a wavelength of light (e.g. color) in an image that may include an object of a particular color and size relative to a remainder of the image. For example, where the tube or coaxial arrangement of tube devices 170 includes a component, such as a stylet or an intubation tube, or components thereof, of a specific color, the 2nd spectrum range of image 1 from the first image source will be different than in a situation in which a component of either, or neither of the intubation device 250 and the tube or coaxial arrangement of tube devices 170, is not present in the patient 102

(e.g. within the view of the first image source). It will be appreciated that a color of the component of the tube or coaxial arrangement of tube devices 170 may preferably be different than a color of the blade 258 of the laryngoscope provided by the intubation device 250, or as described in more detail with reference to FIG. 16, the color of a tube or a cuff of a laryngeal mask airway (LMA), in order to utilize a spectrum range that is different than the 1st spectrum range. However, in a situation in which the intubation device 250 and the tube or coaxial arrangement of tube devices 170 are of similar colors, the controller 210 may analyze the image 1 from the first image source according to different reference values for a single spectrum range, and thus correlate the value of the single spectrum range of the image 1 to a value of an image area within the image that is occupied by the combination of the intubation device 250 and the tube or coaxial arrangement of tube devices 170.

In the case that the controller 210 determines the 2nd spectrum range of the image 1 is not greater than the 1st reference value for the 2nd spectrum range $\lambda\text{-Ref}_{2A}$, the controller 210 determines in block S1218 if a value for the 1st spectrum range of the image 1 is greater than a reference value $\lambda\text{-Ref}_{Z-1}$ for the 1st spectrum range (e.g. a reference value related to a wavelength corresponding to the 1st spectrum range). The reference value $\lambda\text{-Ref}_{Z-1}$ for the 1st spectrum range may correspond to a value of a spectrum range for an image that includes an image area or number of pixels within the image having a given wavelength that corresponds to an open mouth. For example, the reference value $\lambda\text{-Ref}_{z-1}$ may correspond to a value of pixels that are predominantly red based on a signal strength in a red channel relative to other RGB color per the color channel image analysis previously discussed. According to another aspect of the present disclosure, the reference value $\lambda\text{-Ref}_{z-1}$ for the 1st spectrum range may correspond to a ratio of zones classified as red zones to zones of predominantly other color, or a size of a cluster of zones classified as red zones. The ratio may be based on the zone image analysis in which the image 1 is segmented into zones which are classified respectively according to a predominant color within each zone. In the case of a size of a cluster of zones classified as red zones, the controller 210 may correlate a size within the image 1 of a total group of adjacent zones classified as red zones corresponds to a position of the intubation device 250 within the mouth of the patient 102 proximate to an area of the mouth that is distal relative to a tongue. The reference value $\lambda\text{-Ref}_{z-1}$ may also correspond to minimum area of an image having a particular intensity of light for a given wavelength according to a channel and or zone analysis of the image 1 from the first image source (e.g. the first optical imaging device 260).

In the case that the controller 210 determines the 1st spectrum range of the image 1 is greater than the reference value for the 1st spectrum range $\lambda\text{-Ref}_1$, the controller 210 initiates the intubation device timer $t_D$ in block S1220, and in block S1226, activates a display setting for an intubation device timer $t_D$ parameter. Otherwise, the method of analyzing an image obtained by an optical imaging device 1200 is completed.

Figure 13:
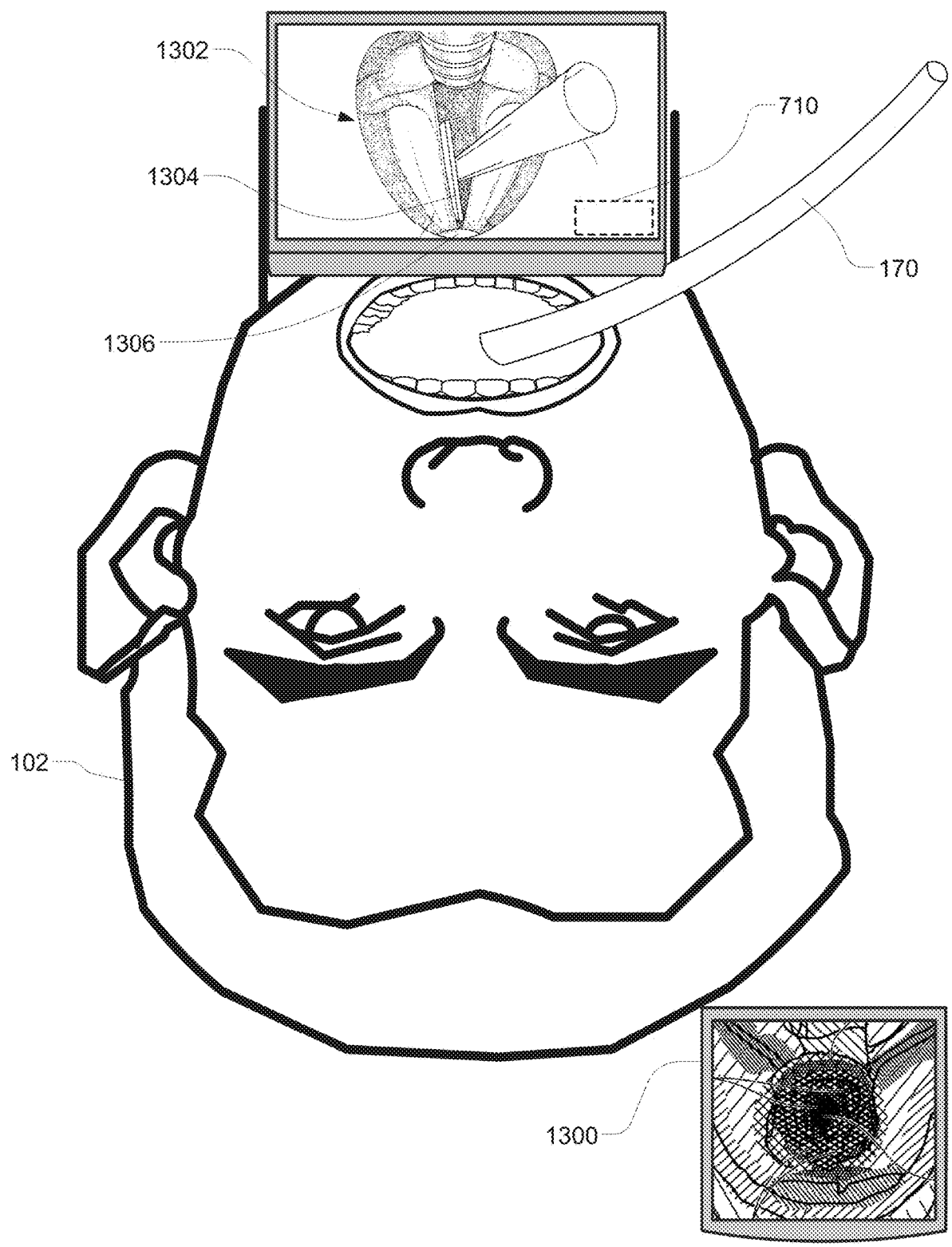
FIG. 13 illustrates a view of a patient utilizing a secondary image source, according to an aspect of the present disclosure.

FIG. 13 illustrates a view of the patient 102 during a procedure utilizing a second image source 1300, according to an aspect of the present disclosure. In particular, FIG. 13 illustrates a situation in which the intubation device 150, such as the intubation device 250 including the first optical imaging device 260, has been positioned in the patient 102, and the tube or coaxial arrangement of tube devices 170 has progressed to a position in the patient 102, as viewed by the first optical imaging device 260 and displayed on the image display device 140. According to an aspect of the present disclosure, the tube or coaxial arrangement of tube devices 170 may include a stylet as or other optical imaging device that provides a second image source which is displayed on an additional image display device 1300. Thus, the tube or coaxial arrangement of tube devices 170 may include a component defining a second optical imaging device that obtains an image 2 of an area encompassed by a field of view of the component of the tube or coaxial arrangement of tube devices 170. The image display device 140 may be in communication with the additional image display device 1300 by wireless connection (e.g. Wi-Fi, Bluetooth, NFC), or via a computing device in communication with the additional image display device 1300.

As illustrated in FIG. 13, an end of the tube or coaxial arrangement of tube devices 170 is positioned distally relative to first optical imaging device 260 and proximal to a larynx 1302 of the patient. Accordingly, FIG. 13 illustrates a situation in which the controller 210 may determine in block S1220, that the 2nd spectrum range of the image 1 is greater than the 1st reference value $\lambda\text{-Ref}_{2A}$ for the 2nd spectrum range. In effect, the controller 210 detects at least the presence of the tube or coaxial arrangement of tube devices 170 with the view of the second optical imaging device 260. Thus, FIG. 13 illustrates an example of situation in which the controller 210 may operate the image display device 140 in accordance with the second image source algorithm 1400.

Figure 14:
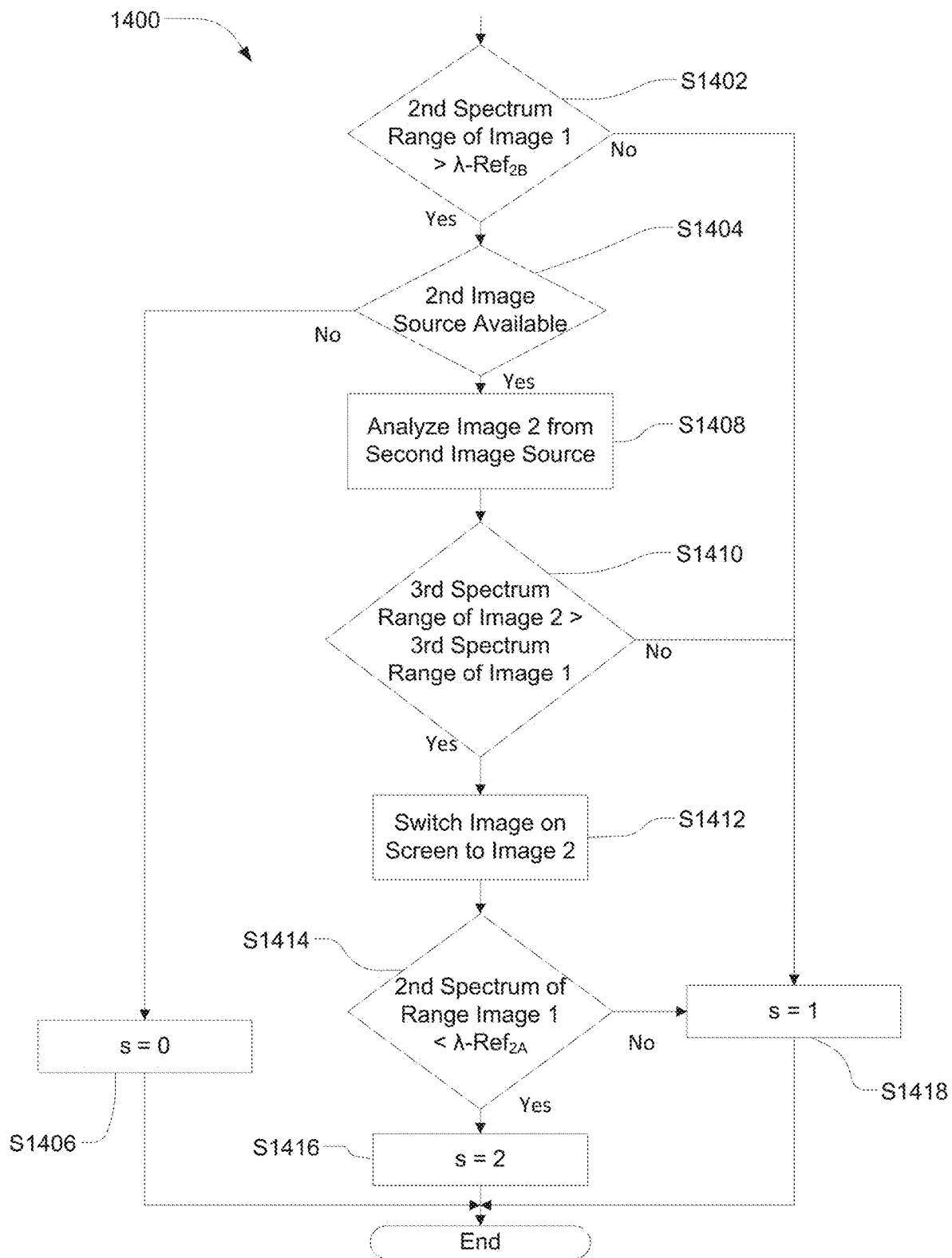
FIG. 14 is an algorithmic flowchart illustrating a method of analyzing an image of a second image source, according to an aspect of the present disclosure.

FIG. 14 is an algorithmic flowchart illustrating a method of analyzing an image of a second image source 1400, according to an aspect of the present disclosure. The foregoing discussion refers to the intubation device 250 and tube or coaxial arrangement of tube devices 170 illustrated in FIGS. 1A, 1B, and 13. However, it will be appreciated that the image display device 140 may perform any of the operations described herein, as provided in combination with different types of intubation devices and tube or tube assemblies including various types of optical imaging devices, including devices which provide images based on light, heat, or other signatures of a surrounding area that may be represented visually.

In block S1402, the controller 210 determines if the value for the second spectrum range of image 1 from the first image source according to the image analysis in block S1204, is greater than $\lambda\text{-Ref}_{2B}$ (i.e. a reference value B of the set of reference values related to a wavelength corresponding to the 2nd spectrum range). Accordingly, the controller 210 determines if the tube or coaxial arrangement of tube devices 170 occupies an area of the image 1 which corresponds to an area of the image 1 that the tube or coaxial arrangement of tube devices 170 would cover, given a color or intensity of color of the tube or coaxial arrangement of tube devices 170, if the tube or coaxial arrangement of tube devices 170 was in a position in which an optimal view of the patient 102 for completing the procedure may be a view from the stylet of the tube or coaxial arrangement of tube devices 170 (e.g. a certain distance from the larynx 1302 of the patient 102).

If the second spectrum range of image 1 is greater than $\lambda\text{-Ref}_{2B}$, in block S1404, the controller 210 determines if a second image source is available. Accordingly, in a situation in which the tube or coaxial arrangement of tube devices 170 does not include the video stylet 172 or other optical imaging device, the controller 210 will set the algorithmic variable (s) equal to zero and the method of analyzing a second image ends. On the other hand, if there is a second image source available, the controller 210 will analyze an image 2 of the second image source in block S1410. For example, the controller 210 will analyze the image being displayed on the additional video display unit 1300 of FIG. 13, and in block S1410 compares results of the analysis of image 2 with a current image analysis of image 1. It will be appreciated that the first image source (e.g. the first optical imaging device 260), remains active and transmits an image of an area in a respective field of view, continuously for analysis at any time during a period in which image display device 140 is operated according to the method of operating a video display 400 described herein.

The controller 210 will switch the image displayed on the screen 208 of the image display device 140 in block S1412, where the controller 210 determines in block S1410 that a value for a 3rd spectrum range of the image 2 from the second image source (e.g. an optical imaging device provided by the video stylet 172 of the tube or coaxial arrangement of tube devices 170), is greater than a value for a 3rd spectrum range of the image 1 from the first image source (e.g. the first optical imaging device 260). This may occur where the second image source has an unobstructed view of a part of the larynx 1300, such as vocal cords 1304 (false or true), occupying an area of the image 2 that would be advantageous for an operator to view vs. a view of the patient 102 from the first image source.

The criteria for block S1410 is preferably based on a reference value related to a wavelength corresponding to the 3rd spectrum range. Alternatively, a combination of landmark recognition and an image analysis for the 3rd spectrum range can be utilized to determine the image displayed by the image display device 140. For example, the controller 210 may determine a common landmark, such as an epiglottis 1306 can be recognized in both the image 1 and the image 2, can be utilized to determine the image displayed by the image display device 140.

In addition to switching from image 1 to image 2, the controller 210 may operate the image display device 140 according the screen information template setting algorithm 500 with respect to the image 2. Accordingly, templates for various types of information related to a period during a procedure corresponding to when, for example, the tube or coaxial arrangement of tube devices 170 is positioned in the patient 102 (e.g. in a trachea of the patient).

In block S1416, the controller 210 determines if the value for the 2nd spectrum range of image 1 from the first image source is less than the 1st reference value $\lambda\text{-Ref}_{2A}$ for the 2nd spectrum range. Determining the value for the 2nd spectrum range of image 1 after the controller 210 has switched to the image 2 may correspond to a situation in during the procedure where the intubation device 250 or a component of the tube or coaxial arrangement of tube devices 170 has been removed from the patient 102. The controller 210 will set the algorithmic variable (s) to a value of 2 where the value of the 2nd spectrum of image 1 is less than the 1st reference value $\lambda\text{-Ref}_{2A}$ for the 2nd spectrum. On the other hand, where the controller 210 determines the conditions of block S1402, block S1410, or block S1414 are not present, the controller 210 sets the algorithmic variable (s) to a value of 1.

Figure 15:
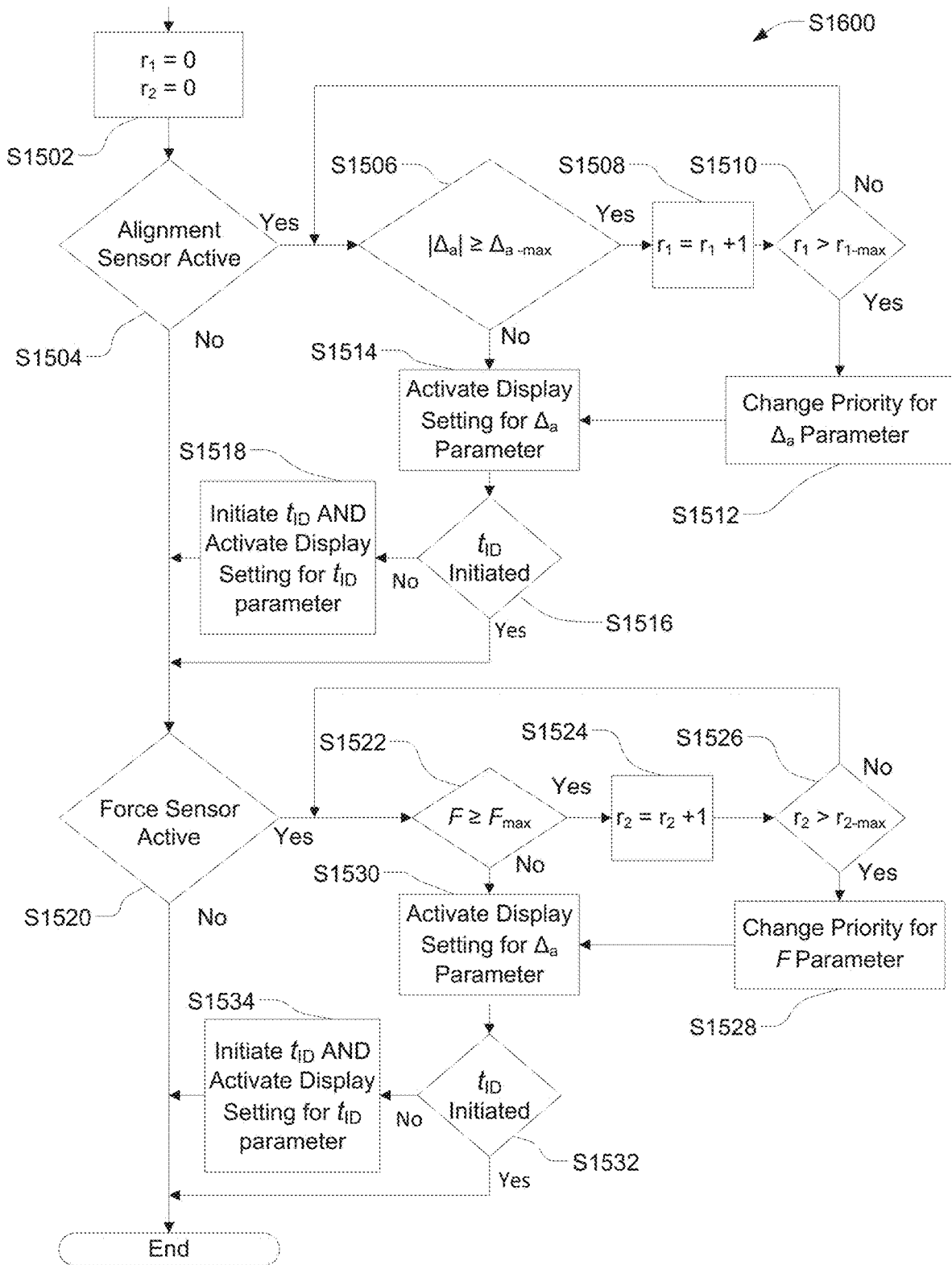
FIG. 15 is an algorithmic flowchart illustrating a method of analyzing a force applied to a patient, according to an aspect of the present disclosure.

FIG. 15 is an algorithmic flowchart illustrating a method of analyzing a force applied to a patient 1500, according to an aspect of the present disclosure. In block S1502 the controller 210 sets a first counter $r_1$ and second counter $r_2$ equal to 0. In block S1504, the controller 210 determines if a sensor, for example the first position sensor 212 or the second position sensor 216 that determines an alignment, or provides data that alone or in combination with data from another source can be used to calculate an alignment of the image display device 140, is active. It will be appreciated that the alignment of the image display device 140 may correspond to an alignment of a device attached to the image display device 140, such as the intubation device 250, for example. Accordingly, a criteria for evaluating the alignment of the image display device 140 may be based on a corresponding alignment of a device to which the image display device 140 is attached.

In block S1506, the controller 210 determines if an alignment deviation $\Delta_a$ is greater than a maximum alignment deviation $\Delta_{a\text{-}max}$ based on a reading from the first position sensor 212 or the second position sensor 216. In block S1508, the controller 210 increments the first counter $r_1$ by a value of 1. In block S1510, the controller 210 determines if a current value of the first counter $r_1$ is greater than a first counter threshold value $r_{1\text{-}max}$ that may be a pre-determined value, a default value, or a value set by an operator as part of the operator's user profile. If the first counter $r_1$ is greater than the first counter threshold value $r_{1\text{-}max}$, indicating that the image display device 140 has not been aligned for a predetermined period of time, the controller 210 may, in block S1512, change a priority for an alignment deviation $\Delta_a$ parameter. On the other hand, if the first counter $r_1$ is determined in block S1510 not to be greater than the first counter threshold value $r_{1\text{-}max}$, the alignment of the image display device 140 is evaluated in block S1506.

A change to the priority of the alignment deviation $\Delta_a$ parameter may be delayed in block S1508 and block S1510. Thus, a situation which could be considered as a false positive for changing the priority of the alignment deviation $\Delta_a$ parameter, such as when the image display device 140 is only momentarily not within the range corresponding to the maximum alignment deviation $\Delta_{a\text{-}max}$, can be avoided. However, the first counter threshold value $r_{1\text{-}max}$ may be set by an operator or the controller 210 for certain operating conditions, to vary a sensitivity for changing display settings based on the alignment deviation $\Delta_a$. Thus, the display settings can be tailored to a particular type of procedure that is particularly short for which an alignment of the image display device 140, or device attached thereto, must strictly be within the maximum alignment deviation $\Delta_{a\text{-}max}$, such that any deviation therefrom may be detrimental to completion of the procedure and/or comfort level of patient.

In block S1514, the controller 210 activates display setting for the alignment deviation $\Delta_a$ parameter, and in block S1516, the controller 210 determines if the intubation device timer $t_{ID}$ has been initiated. Accordingly, if an optical imaging device, for example, the optical imaging device 260 of the intubation device 250, is not operating correctly or is unavailable, or the controller 210 cannot analyze an image from the optical imaging device, a time related to when the intubation 250 is to be positioned in the patient 102, can be recognized, tracked, and displayed on the screen 208 of the image display device 140 for an operator to read. For example, in a situation where the patient 102 has put something their mouth that leaves a residue of a certain color that inhibits the recognition of a spectrum range used to determine various conditions, the intubation device timer $t_{ID}$ can still be initiated when image display device 140, and for example the intubation assembly 200 of FIG. 2, is in a position relative to the patient corresponding to step in a procedure being performed. As a result, the controller 210 initiates intubation device timer $t_{ID}$ and activates the display setting for the parameter corresponding to the intubation device timer $t_{ID}$, where the intubation device timer $t_{ID}$ is determined to not have been initiated in block S1516.

In block S1520, the controller 210 determines if a force sensor, for example force sensor 218, is active, and in block S1522, determines if a force detected F is greater than a maximum force value $F_{max}$. In block S1524, the controller 210 increments the second counter $r_2$ by a value of 1. In block S1526, the controller 210 determines if a current value of the second counter $r_2$ is greater than a second counter threshold value $t_{2-max}$ that may be a pre-determined value, a default value, or a value set by an operator as part of the operator's user profile. If the second counter $r_2$ is greater than the second counter threshold value $r_{1-max}$, indicating that a force proportional to a force, pressure, or moment applied to an external object, such as a body part of patient 102, has exceeded the maximum force value $F_{max}$ for a period of time that may be detrimental to the completion or a procedure of the comfort level of patient. On the other hand, if the first counter $r_2$ is determined in block S1526 not to be greater than the second counter threshold value $r_{2-max}$, the force detected by the force sensor 218 is re-evaluated in block S1522.

A change to the priority of the force F parameter may be delayed in block S1524 and block S1526. Thus, a situation which could be considered as a false positive for changing the priority the force F parameter, such as when a force greater than the maximum force value $F_{max}$ is only momentarily applied may be avoided. However, the second counter threshold value $r_{2-max}$ can be set by an operator or the controller 210 for certain operating conditions, to vary a sensitivity for changing display settings based on the detected force F. Thus, the display settings can be tailored to a particular type of procedure that is particularly short or for which the patient 102 may be particularly sensitive to forces being applied by instruments or devices used to complete the procedure. Accordingly, the image display device 140 operates as a warning system of varying sensitivities according to a procedure being performed, a pain tolerance of a patient, or a standard setting by a regulating authority.

In block S1530, the controller 210 activates the display setting for the force F parameter, and in block S1532, the controller 210 determines if the intubation device timer $t_{ID}$ has been initiated. The controller 210 initiates intubation device timer $t_{ID}$ and activates the display setting for the parameter corresponding to the intubation device timer $t_{ID}$ where the intubation device timer $t_{ID}$ is determined to not have been initiated in block S1534. Accordingly, if an optical imaging device, for example, the optical imaging device 260 of the intubation device 250, is not operating correctly or is unavailable, or the controller 210 cannot analyze an image from the first optical imaging device 260, a time related to when the intubation device 250 is to be positioned in the patient 102, can be recognized, tracked, and displayed on the screen 208 of the image display device 140 for an operator to read.

Figure 16:
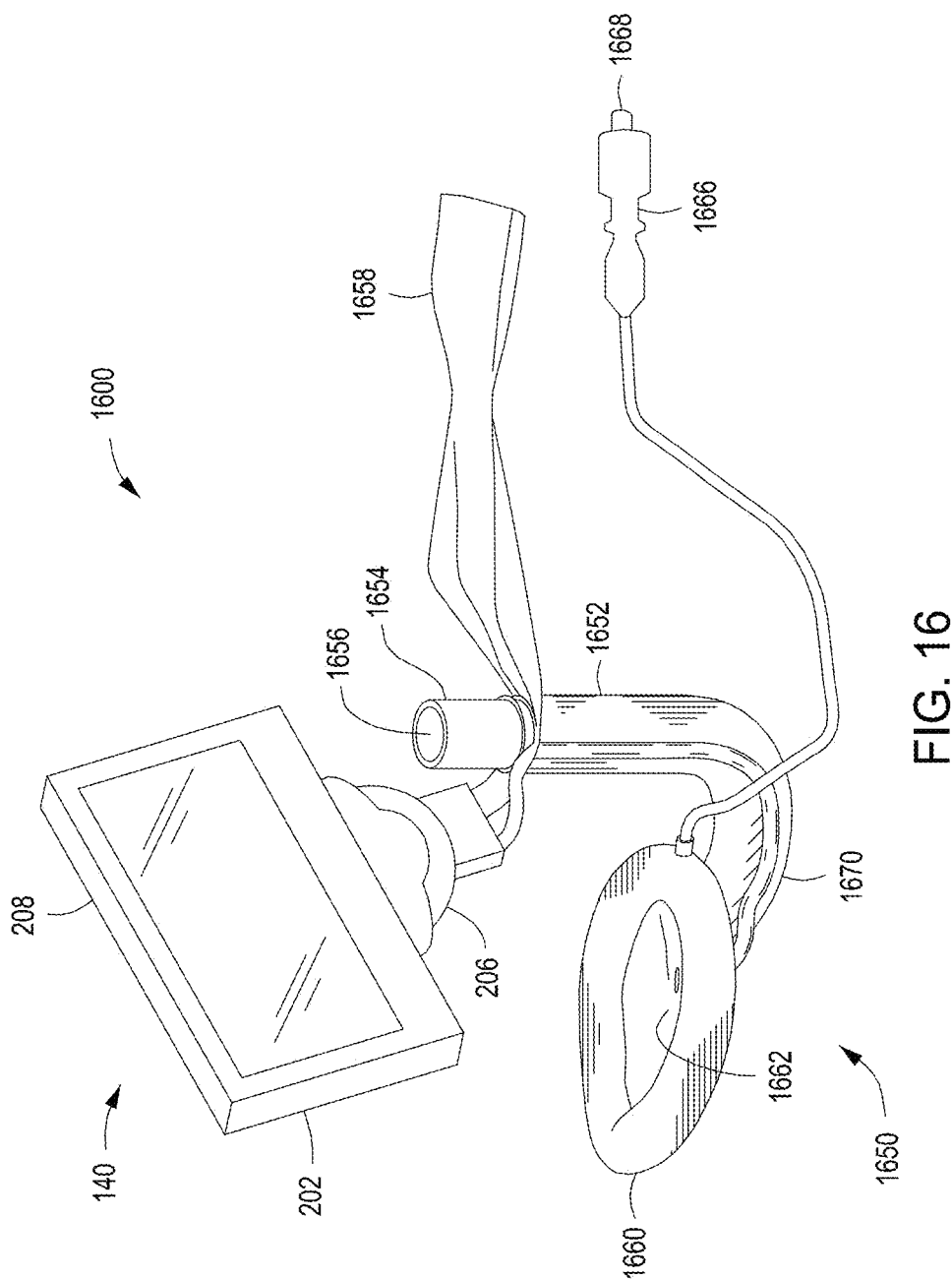
FIG. 16 illustrates an intubation device, according to an aspect of the present disclosure.

FIG. 16 illustrates an intubation device assembly 1600, according to an aspect of the present disclosure. The intubation device assembly 1600 includes the image display device 140 and an intubation device 1650, such as a laryngeal mask airway. The intubation device 1650 includes a main conduit 1652 that extends from a proximal end 1654 including a proximal aperture 1656, to a distal aperture 1658 in a cuff 1660. The cuff 1660 defines a bowl 1662 in fluid communication with the distal aperture 1658, and in fluid communication with an inflation conduit 1664. A pilot balloon 1666 and valve 1668 are attached to an end of the inflation conduit 1664. A first optical imaging device 1670 of the intubation device 1650 may include least one channel, such as a fiber optic channel capable of transmitting an image, extending along the main conduit 1664 into the bowl 1662.

During a procedure, the intubation device 1650 may be positioned in the patient 102, the bowl 1662 positioned facing a laryngeal opening of the patient 102, and the distal aperture 1658 substantially aligned with the laryngeal opening. An optical imaging device such as the video style 172 may be advanced through the main conduit 1652, through the distal aperture 1658, and past the vocal cords of the patient 102. The video style 172 may therefore provide an optical imaging device to provide a second image source which may provide the image 2 that is switched to and displayed on the screen 208 of the image display device 140 in block S1414. Subsequently, a tube including a cuff (e.g. an endotracheal tube) may be advanced over the endoscope through the main conduit 1652 and into the trachea of the patient 102.

Alternatively, the endoscope, as guided by the main conduit 1652 of the intubation device 1650, can be used to guide a deployment of a cuffless tube placed over the endoscope, into the trachea. The tube with the cuff can then be guided over the cuffless tube through the main conduit 1652 and distal aperture 1658 into the trachea. It will be appreciated that other methods of utilizing a passage defined by the main conduit 1652 and the distal aperture 1658 of the intubation device 1650 to advance a tube with a cuff (e.g. and endotracheal tube such as a specialized endotracheal tube to which a stabilizer bar can be attached) into the trachea, may be performed.

The image display device 140 may be connected to a connector 1672 of the intubation device 1650 and the controller 210 connected to the first optical imaging device 1670. Accordingly, any of the methods described herein with respect to the image display device 140 may be carried out with the intubation device assembly 1600.

Figure 17:
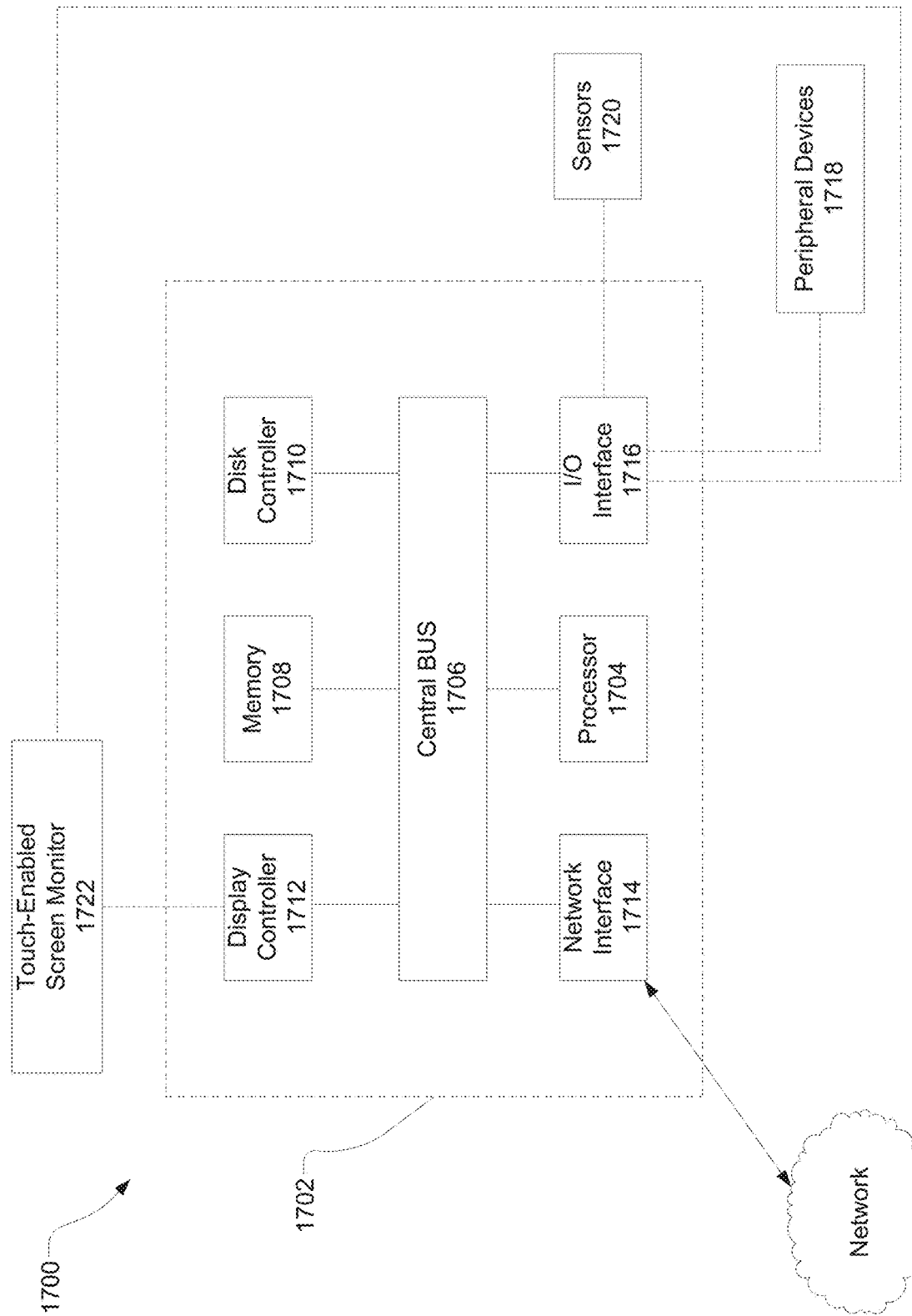
FIG. 17 illustrates a general-purpose computer system, according to an aspect of the present disclosure.

FIG. 17 illustrates a general-purpose computer system 1700, according to an aspect of the present disclosure. The general-purpose computer system 1700 includes or is configured to access one or more computer-accessible media, and includes a computing device 1702 with exemplary hardware incorporated therein. According to an aspect of the present disclosure, the controller 210 of the image display device 140 may include or be defined by the computing device 1702, and the exemplary hardware illustrated in FIG. 17 may implement and/or execute the processes, algorithms and/or methods described in the present disclosure.

The computing device 1702 may include a processor 1704 with one or more processors (which may be referred herein singularly as the processor 1704 or in the plural as the processors 1704) coupled via a central BUS 1706 or other type of I/O interface, to a memory 1708. The computing device 1702 may further include a disk controller 1710, a display controller 1712, a network interface 1714, and an I/O interface 1716 coupled to the central BUS 1706.

In various aspects, the processor 1704 of the computing device 1702 may be a uniprocessor system including one processor, or a multiprocessor system including several processors (e.g., two, four, eight, or another suitable number). The processors 1704 may be any suitable processors, including application specific processors (ASP), capable of executing instructions. As another example, in various aspects, the processor(s) may be general-purpose or embedded processors implementing any of a variety of instruction set architectures (ISAs), such as the x86, PowerPC, SPARC, or MIPS ISAs, or any other suitable ISA. In multiprocessor systems, each of the processors 1704 may commonly, but not necessarily, implement the same ISA.

According to an aspect of the present disclosure, the processor 1704 may include a logic device for augmenting or fully implementing the methods and algorithms of the present disclosure. Such a logic device may include, but is not limited to, an application-specific integrated circuit (ASIC), a field programmable array (FPGA), a generic-array of logic (GAL), and their equivalents. Further, general-purpose computer system 1700 may benefit from parallel processing capabilities of a multi-cored central processing unit (CPU).

The system memory 1708 may be configured to store instructions and data accessible by the processor(s) 1704. In various aspects, the memory 1708 may be implemented using any suitable memory technology, such as static random access memory ("SRAM"), synchronous dynamic RAM ("SDRAM"), nonvolatile/Flash®-type memory, or any other type of memory (e.g., ROM, EPROM, EEPROM, DRAM, and their equivalents). Program instructions and data implementing one or more desired functions, such as those methods, techniques and data described above, may be stored within the memory 1708 as code and data.

In some aspects, the memory 1708 may be one aspect of a computer-accessible medium configured to store program instructions and data as described above for implementing aspects of the corresponding methods and apparatus. However, in other aspects, program instructions and/or data may be received, sent, or stored upon different types of computer-accessible media. Generally speaking, a computer-accessible medium may include non-transitory storage media or memory media, such as magnetic or optical media, e.g., disk or DVD/CD controller coupled to the computing device 1702 via the central BUS 1706, an in particular via the disk controller 1710. A non-transitory computer-accessible storage medium may also include any volatile or non-volatile media, such as RAM (e.g., SDRAM, DDR SDRAM, RDRAM, SRAM, etc.), ROM, etc., that may be included in some aspects of the computing device 1702 as the memory 1708 or another type of memory.

Further, a computer-accessible medium may include transmission media or signals, such as electrical, electromagnetic or digital signals, conveyed via a communication medium, such as a network and/or a wireless link, such as those that may be implemented via the network interface 1714. Portions or all of multiple computing devices, such as those illustrated in FIG. 17, may be used to implement the described functionality in various aspects; for example, software components running on a variety of different devices and servers may collaborate to provide the functionality. In some aspects, portions of the described functionality may be implemented using storage devices, network devices or special-purpose computer systems, in addition to or instead of being implemented using general-purpose computer systems. The term "computing device," as used herein, refers to at least all these types of devices and is not limited to these types of devices.

The network interface 1714 may be configured to allow data to be exchanged between the computing device 1702 and other device or devices attached to a network or networks, such as other computer systems or devices, for example. In various aspects, the network interface 1714 may support communication via any suitable wired or wireless general data networks, such as types of Ethernet networks, for example. Additionally, the network interface 1714 may support communication via telecommunications/telephony networks, such as analog voice networks or digital fiber communications networks, via storage area networks, such as Fibre Channel SANs (storage area networks), or via any other suitable type of network and/or protocol.

In one aspect, the central BUS 1706 may be configured to coordinate I/O traffic between the processor(s) 1704, the memory 1708, the network interface 1714, and any peripherals 1718 which may include, for example, the first connector 222, the second connector 254, the first optical imaging device (260, 1670), and any other devices that may transmit data and receive instructions from the I/O interface 1716. The I/O interface 1716 is further provided for inputting signals and/or data from the peripherals 1718, the sensors 1720, and a touch screen monitor 1722 of the image display device 140. The sensors 1720 may include the proximity sensor 114, the $O_2$ sensor 116, the first position sensor 212, the second position sensor 216, the force sensor(s) 218, and may also include the first optical imaging device (260, 1670).

Results of processing in accordance with the present disclosure can be displayed via the display controller 1712 to the touch screen monitor 1722 of the image display device 140 which provides a use interface. The screen 208 of the image display device 140 may provide a touch sensitive interface of the touch-screen monitor 1722 for providing a command/instruction interface. The display controller 1712 may include at least one graphic processing unit, which can be provided by a plurality of graphics processing cores, for improved computational efficiency.

In some aspects, the central BUS 1706 may perform any necessary protocol, timing or other data transformations to convert data signals from one component (e.g., the memory 1708) into a format suitable for use by another component (e.g., the processor 1704). In some aspects, the central BUS 1706 may include support for devices attached through various types of peripheral buses, such as a variant of the Peripheral Component Interconnect (PCI) bus standard or the Universal Serial Bus (USB) standard, for example. In some aspects, the function of the central BUS 1706 may be split into two or more separate components, such as a north bridge and a south bridge, for example. Also, in some aspects some or all of the functionality of the central BUS 1706, such as an interface to the memory 1708, may be incorporated directly into the processor 1704.

It should also be appreciated that the systems in the figures are merely illustrative and that other implementations might be used. Additionally, it should be appreciated that the functionality disclosed herein might be implemented in software, hardware, or a combination of software and hardware. Other implementations should be apparent to those skilled in the art.

Each of the operations, processes, methods, and algorithms described in the preceding sections may be embodied in, and fully or partially automated by, code modules executed by at least one computer or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any in any type of non-transitory computer storage such as, e.g., volatile or non-volatile storage.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

What is claimed is:

1. A method of approximating a position of an oxygen mask during a procedure, the method comprising:
    detecting a presence of the oxygen mask based on a signal from a sensor or through an observation through an optical imaging device;
    determining, via the sensor or the optical imaging device, whether the oxygen mask is close to or on a patient for supplying oxygen to the patient;
    detecting, via the sensor or the optical imaging device, a removal of the oxygen mask from the patient to stop supplying oxygen to the patient;
    initiating, via one or more processors, a desaturation timer in response to the sensor or the optical imaging device detecting the removal of the oxygen mask from the patient;
    operating, via the one or more processors, an image display device to display a parameter for the oxygen desaturation timer.

2. The method according to claim 1, wherein the sensor is a proximity sensor.

3. The method according to claim 2, further comprising:
    detecting a first distance between the proximity sensor and the oxygen mask;
    comparing whether the first distance is less than or equal to a first distance threshold to determine whether the oxygen mask is on the patient.

4. The method according to claim 3, further comprising:
    detecting whether the oxygen mask is stationary when the oxygen mask is on the patient; and
    resetting the oxygen desaturation timer when the oxygen mask is stationary.

5. The method according to claim 3, further comprising:
    setting, via the one or more processors, a second distance threshold to avoid initiating the oxygen desaturation timer where the oxygen mask has been slightly adjusted and not fully removed from the patient; and
    initiating, via the one or more processors, the oxygen desaturation timer when the first distance is greater than the second distance threshold.

6. The method according to claim 3, further comprising:
    determining, where the oxygen mask has moved from the patient, whether the oxygen mask has been slightly adjusted or fully removed from the patient by comparing the oxygen mask distance to the second threshold distance; and
    initiating, via the one or more processors, the oxygen desaturation timer when the oxygen mask distance is greater than the second distance threshold.

7. The method according to claim 6, further comprising:
    determining if the mask has been put back on the patient and is stationary by comparing a signal from the proximity sensor and the second distance threshold; and
    resetting the oxygen desaturation timer when the oxygen mask has been put back on the patient.

8. The method according to claim 1, wherein detecting the removal of the oxygen mask from the patient comprises determining a reduction in pressure in an oxygen supply line to the oxygen mask via a pressure sensor that registers the reduction in pressure in the oxygen supply line when the oxygen mask is removed from the patient.

9. The method according to claim 1, further comprising:
    comparing, via the one or more processors, the oxygen desaturation time to an oxygen desaturation maximum time corresponding to an elapsed time since the mask was removed from the patient, where the parameter for the oxygen desaturation timer is displayed first and most often based on a respective priority when the oxygen desaturation time is greater than the oxygen desaturation maximum time.

10. The method according to claim 9, further comprising changing data display settings and the priority of the oxygen desaturation timer parameter when the oxygen desaturation timer is greater than or equal to the oxygen desaturation maximum time.

11. The method according to claim 1, where the parameter for the oxygen desaturation timer changes from a numeral or time value to a text value, or to a numeral or time value and a text value.

12. The method according to claim 1, wherein the desaturation timer is implemented in a standalone image display device.

13. The method according to claim 1, wherein the image display device wirelessly receives a desaturation time for displaying.

14. The method according to claim 1, wherein the desaturation timer is integrated with an anesthesia machine.

* * * * *